US006284542B1

(12) United States Patent
Clark et al.

(10) Patent No.: US 6,284,542 B1
(45) Date of Patent: Sep. 4, 2001

(54) OXIDATIVE METABOLISM IN SMOOTH MUSCLE CELLS: METHODS AND MATERIALS RELATING THERETO

(75) Inventors: Joseph F. Clark, Oxford; Thomas A. D. Cadoux-Hudson, Burford, both of (GB)

(73) Assignee: Medical Research Council, London (GB)

( * ) Notice: Subject to any disclaimer, the term of this patent is extended or adjusted under 35 U.S.C. 154(b) by 0 days.

(21) Appl. No.: 09/571,932

(22) Filed: May 16, 2000

Related U.S. Application Data

(62) Division of application No. 09/174,581, filed on Oct. 19, 1998, now Pat. No. 6,080,385, which is a continuation of application No. PCT/GB97/01086, filed on Apr. 18, 1997.

(30) Foreign Application Priority Data

| Apr. 18, 1996 | (GB) | 9608046 |
|---|---|---|
| May 24, 1996 | (GB) | 9610915 |
| Feb. 7, 1997 | (GB) | 9702509 |

(51) Int. Cl.[7] .................. G01N 31/00; G01N 33/18; G01N 33/48; A61B 10/00
(52) U.S. Cl. .................. 436/17; 436/62; 436/63; 600/562
(58) Field of Search .................. 436/17, 62, 63; 600/562

(56) References Cited

U.S. PATENT DOCUMENTS 4,445,500   5/1984   Osterholm .................. 604/52

OTHER PUBLICATIONS

Dissertion Abstracts International B Science And Engineering, vol. 42, No. 12, 1982, Washington DC USA, p.4732 XP002039256, M.E. Rosenfeld et al.: Studies of oxidative metabolism in vascular smooth muscle. see whole document.

FASB Journal, vol. 11, No. 3, Apr. 6, 1997, New Orleans LO USA, P. a59 XP002039152 G. J. Pyne et al.: "Vascular smooth muscle oxidation metabolism during vasospasm" see whole document.

Chemical Abstracts 128: 152332, "Peripheral Markers in Testing Pathophysiological Hypotheses and Diagnosing Alzheimer's Disease" (1992).

*Primary Examiner*—Frederick Krass
(74) *Attorney, Agent, or Firm*—Nixon & Vanderhye P.C.

(57) ABSTRACT

The application concerns oxidative metabolism in smooth muscle cells and to methods and materials related thereto. Provided is a method which is a medium suitable for the support of oxidative metabolism comprises: 1) incubating a cell or tissue sample with a specimen derived from a patient wherein the sample comprises smooth muscle cells; 2) measuring a marker of oxidative metabolism of the cell or tissue sample; and 3) detecting an increase in oxidative metabolism which is not attributable to a contractile demand for ATP, such as an increase in oxidative metabolism being indicative of the existence in a patient of an agent or combination of agents able to cause an increase in oxidative metabolism in smooth muscle cells.

11 Claims, 14 Drawing Sheets

OXIDATIVE METABOLISM IN SMOOTH MUSCLE CELLS: METHODS AND MATERIALS RELATING THERETO

This application is a divisional of U.S. Ser. No. 09/174,581, filed Oct. 19, 1998, now U.S. Pat. No. 6,080,385, which is a continuation of PCT/GB97/01086, filed Apr. 18, 1997.

The present invention relates to oxidative metabolism in smooth muscle cells and to methods and materials relating thereto.

In particular, the present invention relates to methods and materials relating, for example, to (i) diagnosis of the existence or onset of chronic vasospasm/vasoconstriction (ii) monitoring treatment of chronic vasospasm/vasoconstriction (iii) identifying new drugs effective in the treatment of chronic vasospasm/vasoconstriction (iv) the elucidation of agents ("spasminogens") causing chronic vasospasm/vasoconstriction.

Vasospasm/vasoconstriction represents a significantly preventable cause of morbidity and death. Vascular smooth muscle (VSM) is able to maintain tension for extended periods at low energy cost (the phenomena is known as "latch"). This is essential for the autonomous and continuous regulation of blood flow to the organs etc. However in vasospasm/vasoconstriction, there is an abnormal contraction of the blood vessels to a vascular bed combined with the blood vessels having a diminished ability to relax. This restricts the blood flow and in consequence the oxygen supply. A variety of vascular beds including eg cardiac, mesenteric, placental, uterine and cerebral may be affected with consequent serious clinical implications such as organ damage, stroke, death or miscarriage (Rajani, R. M., B. V. Dalvi, S. A. D'Silva, Y. Y. Lokhandwali and P. A. Kale (1991) Postgrad. Medical Journal 67 (783) 78–80 and Gewertz B. L. and C. K. Zarins (1991) J. Vasc. Surg. 14 382–385.)

The term "vasospasm" is generally used in relation to contraction of the blood vessels particularly associated with the brain. In contrast, the term "vasoconstriction" is generally used in relation to constrictions of the blood vessels associated with organs other than the brain. Hereafter, where the term vasospasm is used it should not be interpreted solely as a reference to a vascular spasm associated with the brain unless the context otherwise demands such interpretation.

The invention of the present application is disclosed with reference to a number of clinical conditions linked with abnormal metabolism associated with vasospasm/vasoconstriction, namely: cerebral vasospasm in consequence of sub-arachnoid haemorrhage; pre-eclampsia and Alzheimer's disease. Conditions other than those specifically named will be known to those skilled in the art as being associated with chronic spasm/constriction of smooth muscle cells, such as chronic vasospasm/vasoconstriction.

Cerebral vasospasm occurs as a result of a sub-arachnoid haemorrhage. The haemorrhage strikes without warning, mostly in young adults and affects about 16 in every 100,000 people each year. The condition accounts for about 10% of all cerebrovascular disease.

The arachnoid layer lies between the pia meter (which wraps the brain and closely follows its contours) and the outermost dural layer. It comprises two arachnoid membranes separated by the sub-arachnoid space which is a cerebral spinal fluid (CSF) filled cavity containing blood vessels which supply oxygen to the brain. Thus, these blood vessels supplying the brain are bathed in CSF. A sub-arachnoid haemorrhage occurs when a blood vessel in the sub-arachnoid space ruptures. Typically the rupture results from an aneurysm. Blood leaks from the vessel into the sub-arachnoid space where it mixes with the CSF.

In 30% of sub-arachnoid haemorrhage patients, the rupture to the blood vessel results in death before the patient reaches the hospital. The remaining 70% survive the initial damage to the blood vessel and are admitted to hospital. In these admitted patients, the damaged vessel constricts to prevent excess blood loss and blood flow is reduced. This initial constriction in the acute phase of the condition is known as a vasoconstriction and is a part of the normal vessel repair response process. With the constriction, the repair of the rupture commences with the formation of a clot. In some patients (about 60% of those admitted) the vessel eventually re-dilates following occlusion of the rupture and blood flow returns to normal with consequent good clinical outcome and return to good health. Unfortunately, and despite considerable clinical efforts, other patients (the remaining 40% of those admitted) deteriorate. The deterioration may be the result of a vessel re-bleed or hydrocephalus (excess CSF in the cranial vault) and in such circumstances the patient can be treated by surgery and stands a relatively good chance of survival. Alternatively, the deterioration may be due to the delayed onset of prolonged and irreversible vasospasm (hereafter referred to chronic vasospasm). Unless the condition is diagnosed prior to its onset and effectively treated by drug therapy or surgery, it can lead to stroke, brain oedema or death.

In order to prevent the onset of chronic vasospasm in sub-arachnoid haemorrhage patients, one needs to be able to accurately diagnose those patients who are likely to undergo the condition. The presently available diagnostic methods do not allow one to predict the likely onset of chronic vasospasm in sub-arachnoid haemorrhage patients. It is only possible to diagnose the actual presence of chronic vasospasm and this is determined by performing an angiogram in order to determine the cause of the bleed and also to look for evidence of vascular constrictions.

Of the 70% of patients who survive the initial bleed and undergo an angiogram, 60% show evidence of vasospasm. Only 40% of these will actually develop neurological deterioration. However, some patients can develop a delayed neurological deterioration without evidence of angiographic vasospasm, but with reduced blood flow. Therefore, in this group of patients the data suggests that an angiogram is not an accurate method of diagnosing the onset of chronic vasospasm.

There is also a time window for performing successful surgery, as if surgery is performed between 3 and 14 days after sub-arachnoid haemorrhage, the risk of chronic vasospasm actually increases. The results from angiograms are not sufficiently predictive of the optimal time for undertaking surgery.

Thus there is a need for a method which allows one to predict as soon as possible those patients likely to go into chronic vasospasm, such that appropriate and/or required intervention can be initiated within the first three days following the cerebral haemorrhage.

In addition to the absence of suitable diagnostic methods, there is not at present an effective treatment for chronic cerebral vasospasm. To date, the condition is treated by angioplasty to the narrowed artery and by use of the $Ca^{2+}$ antagonist, Nimodipine (Nimotop*, Bayer). However, results have shown that although treatment with Nimodipine produces a small (20%), but significant improvement in clinical outcome for patients, it does not alter the vessel lumen size and therefore does not reverse the constrictive effects of the cerebral vasospasm (Pickard, J. D., G. D. Murray and R. Illingworth (1989) *Brit. Med. Journal* 298 636–642).

Indeed it is possible that the use of calcium antagonists may be counterproductive. The prior art to date indicates that cerebral vasospasm is the result of metabolic failure of the VSM cells and that breakdown products of red blood cells within CSF can alter the energy metabolism of VSM as evidenced by decreases in phosphocreatine and ATP (Kim, P., J. Jones and T. M. Sundt (1992) *J. Neurosurg.* 76 991–996) and an increase in ADP. ADP has been shown to inhibit VSM cross-bridges (Clark J. F., Z. Khuchua, A. V. Kuznetsov, A. E. Boehm and R. Ventura-Clapier (1994) *J. Musc. Res. Cell motil.* 15 432–439 and Clark J. F., G. J. Kemp and G. K. Radda (1995) *J. Theor. Biol.* 173 207–211) and therefore elevated ADP may lead to an inability of vascular smooth muscle (VSM) to relax. This suggestion fits with the observation that a $Ca^{2+}$ antagonist such as (Nimodipine) cannot change the contractile state, as ADP maintained tension is independent of $Ca^{2+}$ (Clark et al., (1994) supra). Therefore the use of anything which results in an elevation of ADP is undesirable. A $Ca^{2+}$ antagonist can decrease cytosolic $Ca^{2+}$. The decrease in cytosolic calcium may lead to an elevation of ADP because of decreased mitochondrial function due to lack of $Ca^{2+}$ stimulation.

Glucocorticoid steroids, antioxidants, anti-prostaglandin agents, endothelin antagonists and other vaso-dilators have all failed to provide any clinical benefits despite initially encouraging animal studies.

Thus there remains a real need for agents effective in the treatment of clinical conditions associated with chronic vasospasm/vasoconstriction, such as cerebral vasospasm following sub-arachnoid haemorrhage.

Investigations into the pathological significance of the metabolic failure in canine basilar arteries after sub-arachnoid haemorrhage showed that the ATP, GTP and PCr content of the arteries diminished rapidly over the 14 days post-haemorrhage, with significant decreases being seen from day 3 (Kim et al., (1992) supra). The same investigators in a study looking at the high energy phosphate levels in the canine cerebral artery during chronic vasospasm, found that the levels of ATP, GTP and PCr were also decreased in these spastic arteries and that the ratios of ATP:ADP, GTP:GDP and PCr:Cr were decreased. Further, total adenine and creatine contents were diminished.

This association between metabolic failure and irreversible VSM cell contraction is supported by observations that: (i) a decrease in ATP leads to a rigor-like status in VSM cells; (ii) exposure of VSM cells to 250 $\mu$M intracellular ADP results in an inability of the cells to relax properly (Clark et al., (1994) supra); and (iii) application of intracellular ADP to contracted VSM cells impairs their ability to relax in a dose dependant manner (Nishye, E., A. V. Somlyo, K. Torok and A. P. Somlyo et al., (1993) *J. Physiol.* 460 247–271).

Thus, the thinking based on the prior art studies to date, is that mitochondria are deficient in the production of ATP, thus decreasing the ATP:ADP ratio and causing a relative increase in cellular ADP levels, there being a failure of the oxidative metabolism. The increased levels in cellular ADP lead to prolonged contraction of the smooth muscle cells and to their inability to relax. The reduction in high energy phosphates was measured in correlation with vasospasm, and indicated that the onset of chronic vasospasm is correlated to a deficiency in high energy phosphates.

However, contrary to the above teachings, the present inventors have made the unexpected and surprising discovery that increased ADP levels in VSM cells following sub-arachnoid haemorrhage is in consequence of an increase in flux through the oxidative metabolism pathway, rather than due to mitochondrial deficiency.

When VSM cells are maximally stimulated under working conditions, oxidative metabolism is double that of the basal rate observed in non-working conditions. Uncoupling mitochondria with an agent such as dinitrophenol causes them to consume oxygen without producing ATP. The maximum rate of oxygen consumption observed in uncoupled mitochondria is 3 times the basal rate.

The present inventors have made the unexpected discovery that if one applies eg CSF supernatant from the sub-arachnoid space of a patient who has suffered a sub-arachnoid haemorrhage, CSF supernatant from Alzheimer's disease patients or sera from pre-eclampsia patients, to a portion (eg. a strip or ring) of porcine carotid artery (which comprises VSM cells) under non-load conditions such that any increase in oxygen consumption observed cannot be due to contraction of the strip (no load means no contractile demand for ATP), there is a significant increase (typically a 6 time increase) in the rate of oxygen consumption as compared to basal rate consumption along with an increase in ATPase. The increase in rate of oxygen consumption develops over several hours, but is clearly evident after only a 1 hour delay and maintained for 5 or more hours.

This discovery is contrary to the teachings of the prior art as discussed above i.e. rather than the respiratory system failing/dying, there is an increase in flux. If, as the prior art teaches, the observed increase in ADP is in consequence of metabolic failure, one would not expect to see an increase in cellular oxygen consumption.

Thus the evidence of the present inventors suggests that in a clinical condition associated with chronic spasm/constriction of smooth muscle cells (eg chronic vasospasm/vasoconstriction as in cerebral vasospasm in consequence of sub-arachnoid haemorrhage, pre-eclampsia and Alzheimer's disease), there is a spasminogen (this term being used to refer to an agent or combination of agents which cause the increase in oxidative metabolism in smooth muscle cells (such as vascular smooth muscle cells leading to chronic vasospasm/vasoconstriction) not attributable to a contractile demand for ATP) present in body fluids such as CSF or blood (in cerebral haemorrhage, blood mixes with CSF in the sub-arachnoid space), which appears to stimulate ATPase eg actinomyosin ATPase in smooth muscle such as VSM and is the likely initiator of chronic spasm/constriction. The mitochondria respond to the increased ATPase activity by consuming increased amounts of oxygen to produce ATP, but are unable to maintain metabolic homeostasis and thus ADP levels increase. The increased levels of ADP appear to be the cause of irreversible spasm/constriction of the blood vessels.

In relation to cerebral vasospasm, research into the nature of the spasminogen currently falls into two groups: (a) indirect vasoactive compounds such as inflammatory compounds (prostaglandins, thromboxanes, leukotrienes, and blood breakdown products); and (b) direct vasoactive compounds such as $Ca^{2+}$ ions, angiotensin and endothelin.

Current theory suggests that in cerebral vasospasm the spasminogen(s) is released into the CSF from the blood, where effects causing constriction of VSM cells are mediated. Endothelin 1 which has been implicated in coronary artery vasospasm (Igarashi K., M. Horimota and T. Takenaka, (1993) *J. Cardiol.* 23 257–262; Davies M. G., M.

L. Klyachkin, J. H. Kim and P. O. Hagen (1993) *J. Cardiovasc. Pharmacol.* 22 Suppl. 8 S348–S351; Chester A. H., G. S. O'Neil, S. P. Allen and T. N. Luu (1992) *Eur, J. Clin. Invest.* 22 210–213) and mesenteric artery vasospasm (Yoshida M., a. Suzuki and T. Itoh (1994) *J. Phsiol. Lond.* 477 253–265) has been proposed as a likely spasminogen although there is also evidence that induction of vasospasm may be mediated by a multitude of compounds (Toyo-oka T., T. Aizawa, N. Suzuki, Y. Hirata, T. Miyauchi, W. S. Chin, M. Yanagisawa, T. Masaki and T. Sugimoto (1991) *Circulation* 83 476–483).

Turning now to pre-eclampsia and Alzheimer's disease.

Pre-eclampsia is the foremost cause of maternal death and iatrogenic prematurity in the UK. It predisposes to intrauterine growth retardation, foetal asphyxia and foetal death. The features of the maternal syndrome are remarkably diverse including hypertension, proteinuria, abnormal clotting and multiple organ dysfunction. Cerebral pathology associated with the syndrome comprises one of the commonest causes of maternal death. Eclampsia, characterised by epileptiform convulsions, is thought to arise from such intense vasoconstriction as to cause focal cerebral ischaemia, even infarction. The origins of the pathology are obscure, but the associated cerebral vasospasm is confirmed by magnetic resonance angiography (Matsuda et al., 1995 Gynecol. Obstet. Invest. 40, 249–252) and computed tomographic imaging. Pathological vasoconstriction which occurs during cerebral vasospasm, is also a component of the hypertension and other problems of pre-eclampsia including, apart from eclampsia itself, the liver dysfunction and foetal distress, which are all characteristic of the syndrome. The diverse features of the syndrome results in the diagnosis of the condition being very subjective and in consequence inherently unreliable. There is a need for more reliable methods which allow one to predict either the likelihood of the condition occurring or the presence of the condition.

Alzheimer's disease is a major cause of memory loss and dementia in elderly people. Depositing of two types of abnormal filaments are characteristic brain lesions seen in Alzheimer's patients: the mainly intraneuronal neurofibrillary tangles which consist of paired helical filaments and the extracellular amyloid fibers and phosphorylation of τ(tau) protein. To date, a firm diagnosis of Alzheimer's disease is made on the basis of the presence of large numbers of these abnormal filamentous structures in the brain.

However the diagnosis can only be carried out in conjunction with major surgery of an invasive nature. Generally this diagnosis is carried out post-mortem. Therefore there is a real need for alternative/additional diagnostic methods which are less invasive.

The discussion above makes it clear that improved diagnostic and treatment methods are needed in relation to certain medical conditions such as chronic cerebral vasospasm, pre-eclampsia and Alzheimer's Disease which are related to the presence of an agent or combination of agents able to cause an increase in oxidative metabolism in smooth muscle cells such as VSM cells and hence an abnormal metabolic state associated with chronic spasm/constriction (eg vasospasm/vasoconstriction).

The present invention provides a new way of both predicting a patient's likelihood of suffering a pathological condition which is in consequence of the presence of an agent or combination of agents able to cause an increase in oxidative metabolism in smooth muscle cells (eg VSM cells) and hence an abnormal metabolic state associated with spasm of smooth muscle cells (such as chronic cerebral vasospasm following from sub-arachnoid haemorrhage; pre-eclampsia, Alzheimer's Disease) and diagnosing a patient as having such a pathological condition and/or abnormal metabolic state. The present invention also provides ways of (i) identifying spasminogens present in biological samples which are critically involved in inducing chronic spasm/constriction; (ii) identifying new drugs for preventing or ameliorating such spasms/constrictions; (iii) monitoring the effectiveness of any treatment administered to a patient to either prevent or ameliorate such spasms/constrictions.

The diagnostic or predictive method comprises:

in a medium suitable for the support of oxidative metabolism incubating a cell or tissue sample with a fluid specimen deriving from a patient, wherein the sample comprises smooth muscle cells;

measuring a marker of oxidative metabolism of the cell or tissue sample and detecting an increase in oxidative metabolism which is not attributable to a contractile demand for ATP, such an increase being indicative of the existence in the patient an agent or combination of agents able to cause an increase in oxidative metabolism in smooth muscle cells not attributable to a contractile demand for ATP.

Where there is in a patient an agent or combination of agents able to cause an increase in oxidative metabolism in smooth muscle cells not attributable to a contractile demand for ATP, the increase in oxidative metabolism may be unusual/abnormal and of clinical significance.

The increase in oxidative metabolism may be significant and sustained. Thus the increase in oxidative metabolism may be of a level represented by an increase in oxygen consumption of about three times or greater. The increase may be represented by an increase in oxygen consumption of approximately five times increase. The increase in oxidative metabolism may be sustainable for greater than one hour, usually several hours, for example for 5 or more hours.

The method can be used to diagnose a patient as having, or predicting that a patient will in future have an abnormal metabolic state (which impacts on the contractile state as metabolism through ADP production will alter the contractile state of smooth muscle cells) characterised by an increase in oxidative metabolism in smooth muscle cells not attributable to a contractile demand for ATP. The sample may comprise vascular smooth muscle cells and the abnormal metabolic state may be associated with chronic vasospasm/vasoconstriction and clinical conditions related thereto. Although species and vascular bed cross-over is perfectly possible and exemplified herein, the vascular smooth muscle cells may be representative of those involved in the suspected existing or predicted vasospasm/vasoconstriction of a vascular bed. The method may be employed in relation to the diagnosis, prognosis, prediction and/or quantification of a medical condition such as pre-eclampsia, Alzheimer's Disease or chronic cerebral vasospasm.

In relation to chronic cerebral vasospasm, if the specimen causes an increase in oxidative metabolism that is not attributable to a contractile demand for ATP (such a specimen may be described as "hot") and is obtained from a patient within the first three days post-haemorrhage this indicates that the patient is at high risk of going into vasospasm. However under such circumstances one would generally re-test eg daily or twice daily within the few weeks post-haemorrhage to monitor changes in the likelihood of developing vasospasm. Risk of vasospasm may increase or recede.

Conversely, if the specimen has no effect on oxidative metabolism (such a specimen may be described as "cold")

this indicates that the patient is not at high risk of going into vasospasm. However, under such circumstances one may wish to regularly re-test the patient (eg. daily or twice daily) within the two weeks post-haemorrhage to monitor changes in the likelihood of developing vasospasm.

The test results will influence the medical or surgical treatment. Generally speaking, where the specimen proves to be "cold" surgery is likely to be safer.

Thus where the specimen is "cold" one may operate irrespective of the timing of surgery with respect to the initial haemorrhage (traditionally one would delay for 14 days before operating, but such delay may be unnecessary where the specimen is cold).

Where the specimen is "hot" the options are to delay operating until such time as a "cold" specimen is obtained, or proceed with surgery in the knowledge that there is an increase in risk of the patient going into vasospasm and that the patient will need to go into an intensive care unit for close observation and treatment.

Generally, where one is wanting to identify a spasminogen (ie an agent or combination of agents able to cause an increase in oxidative metabolism in smooth muscle cells such as VSM cells, not attributable to a contractile demand for ATP) one may be aided by a method which involves in a medium suitable for the support of oxidative metabolism incubating a cell or tissue sample which comprises smooth muscle cells with a specimen thought to contain a said spasminogen and measuring a marker of oxidative metabolism of the cell or tissue sample; and detecting an increase in oxidative metabolism which is not attributable to a contractile demand for ATP, such an increase in oxidative metabolism being indicative of the presence of said spasminogen in the specimen.

The smooth muscle cells may be vascular smooth muscle cells. The vascular smooth muscle cells may be of a type representative of those thought to be affected in vivo by the spasminogen.

The biological specimen may comprise a fraction of a specimen as derived from a patient. Fractions may be derived in accordance with known metabolite or protein purification techniques such as phase separation, electrophoresis, chromatography and mass spectrometry. The method may comprise the additional step of purifying the spasminogen from the biological sample in accordance with protein purification techniques and small molecule purification techniques known in the art.

Thus the invention provides any new spasminogen (an agent or combination of agents able to cause an increase in oxidative metabolism in smooth muscle cells (eg vascular smooth muscle cells) not attributable to a contractile demand for ATP) readily identifiable by use of the methods as herein described.

Spasminogens or patient derived specimens (eg sera) identified as being able to cause an increase in oxidative metabolism in smooth muscle cells eg vascular smooth muscle cells, not attributable to a contractile demand for ATP can be used in the methods herein described to screen for compounds useful as drugs to counter or block the effects of the spasminogen.

Generally where one is wanting to screen compounds for potential efficacy as therapeutic agents the method involves:

in a medium suitable for the support of oxidative metabolism incubating a cell or tissue sample which comprises smooth muscle cells with (a) a specimen, agent or combination of agents known to effect an increase in oxidative metabolism of the cell of tissue sample which is not attributable to a contractile demand for ATP; and (b) a test compound;

measuring a marker of oxidative metabolism; and detecting an absence or reduction of the increase in oxidative metabolism not attributable to a contractile demand for ATP and which is normally effected by the specimen, agent or combination of agents, any such absence or reduction being indicative of the test compound having potential efficacy as a therapeutic agent.

The cell or tissue sample may comprise vascular smooth muscle cells.

The cell or tissue sample can be incubated with the test compound prior to incubation with the specimen, agent or combination of agents. Alternatively, the cell or tissue sample can be incubated with the test compound and specimen, agent or combination of agents substantially simultaneously. In either of these approaches, the absence or reduction of the increase in oxidative metabolism which is not attributable to a contractile demand for ATP, can be detected by comparison to a control test, which is identical except for being without the test compound.

In the alternative, in a medium suitable for the support of oxidative metabolism the cell or tissue sample can be incubated with the specimen, agent or combination of agents prior to incubation with the test compound and for a time sufficient to establish an increase in oxidative metabolism which is not attributable to a contractile demand for ATP. The test compound is then added and one then can measure the marker of oxidative metabolism in order to detect a reduction of the increase in oxidative metabolism which is not attributable to a contractile demand for ATP normally associated with the specimen, agent or combination of agents.

The present invention therefore also provides new compounds and treatment methods identified following use of an approach as herein described and the use of such drugs in the preparation of medicaments for the prevention or treatment of abnormal metabolic or contractile states characterised by an increase in oxidative metabolism in smooth muscle cells (eg vascular smooth muscle cells) not attributable to a contractile demand for ATP. The prevention/treatment may be of a chronic vasospasm/vasoconstriction. The prevention/treatment may be in relation to pre-eclampsia, Alzheimer's Disease or chronic cerebral vasospasm.

Where one is wanting to monitor the effectiveness of any treatment administered to a patient to either prevent or ameliorate an abnormal metabolic state or chronic spasm/constriction (eg chronic vasospasm/vasoconstriction) or symptoms of pre-eclampsia, Alzheimer's Disease or chronic cerebral vasospasm, the method involves carrying out a method of diagnosis as earlier described and repeating the method at one or more appropriately selected time intervals to detect an alteration of the increase in oxidative metabolism which is not attributable to a contractile demand for ATP and wherein a reduction of the increase is indicative of the treatment being therapeutically advantageous.

The incubations can be carried out in any medium suitable for the support of oxidative metabolism. One suitable incubation medium is Krebs buffer with 11 mM glucose and/or 5 mM pyruvate. Another is Krebs-Hensleit buffer containing 0.5 mM $KH_2PO_4$ with either 11 mM glucose or 5 mM pyruvate as the substrate. The incubations may be aerated with $95\%O_2$–$5\%CO_2$. The pH may be 7.4. Other mediums and incubation conditions suitable for the methods described herein are known and available to those skilled in the art.

The cell or tissue sample used may be one which is representative of those involved in the spasm. For example, if the spasm is of vascular smooth muscle, the sample should comprise VSM cells and therefore the tissue sample may comprise a suitable culture of VSM cells or a strip of tissue from eg basilar, carotid, coronary or mesenteric arteries of pigs, guinea pigs or humans, or rat aorta. If one is concerned with measuring spasm associated with a particular organ, one may select the cell culture or tissue accordingly, eg for chronic cerebral vasospasm one may select carotid arteries or basilar arteries and for cardiac vasospasm one may select coronary artery or aorta. In relation to pre-eclampsia one may use cells or tissue samples deriving from the uterine or placental vascular beds or from the umbilical artery.

If one is concerned with spasm of non-vascular smooth muscle cells, the sample should be selected accordingly and the cell culture/tissues may derive from eg intestine endometrium, myocardium, or skeletal muscle tissue. Cell culture samples may be used eg A7RS VSM cells derived from embryonic rat aorta (ECACC, PHLS Centre for Applied Microbiology and Research, Salisbury, Wiltshire, United Kingdom SP4 0JG).

Generally speaking, the specimen may be fluid specimen such as any derivable from a patient (eg. CSF, blood, urine, sera plasma, pentoneal fluid, pericardial fluid, pleural fluid) and which is likely to contain the spasminogen if present. Obviously, the choice of fluid specimen for analysis will be dictated by the nature of the patient's condition, but in many cases the fluid sample will comprise blood or serum. For chronic cerebral vasospasm resulting from sub-arachnoid haemorrhage, the fluid specimen may comprise CSF which has mixed with blood in the sub-arachnoid space in consequence of the haemorrhage.

The marker of oxidative metabolism may be oxygen consumption rate, ATPase activity (see example 6 and Clark, J. F. and Dillon, P. F., 1995 J. Vasc. Res. 32, 24–30), kinase activity ADP concentration (Fisher, M. J., and Dillon, P. F., 1988 NMR in Biomed. 1, 121–126), all of which will increase in line with an increase in oxidative metabolism. An alternative marker of oxidative metabolism is the phosphorylation state of myosin (Dillon, P. F. et al., 1981 Science 211, 495–497) and other suitable markers will be apparent to those skilled in the art. Techniques for measurement of various markers indicating the state of oxidative metabolism are known to those skilled in the art. For example, where one chooses to measure oxygen consumption rate as a marker of oxidative metabolism, the incubation may be carried out in an air-tight vessel incorporating an oxygen sensor for measurement of the oxygen concentration of the incubation solution. Alternatively, one may measure markers such as ATPase activity in the cell or tissue sample, ADP concentration in the model cell or tissue, phosphorylation state of myosin or other contractile proteins associated with myosin in the cell or tissue all in accordance with known techniques and as referred to in the papers stated above.

The incubation period may be any period sufficient to allow detection of an increase in oxidative metabolism. The examples provided herein give those skilled in the art some guidance, but the skilled person would be able to determine an appropriate incubation period. Generally, where the specimen is peripheral blood and the tissue is vascular smooth muscle in the form of a strip of porcine carotid artery an incubation period in excess of 120 mins may be necessary. Where one is concerned with chronic cerebral vasospasm and the specimen is CSF, the incubation period may be shorter than this. Other detailed or chronic analysis may require as long as 2 days. Of course as stated earlier alternatives to the specific form of tissue eg vascular smooth muscle tissue, used to exemplify the discoveries and invention may be employed eg smooth muscle cells from cell culture.

In the above, one is looking for any increase in oxidative metabolism which is not attributable to a contractile demand for ATP. Thus the smooth muscle cells of the sample may be without a contractile demand for ATP ie they are not contracting. Where the smooth muscle cells of the model cell or tissue sample are without a contractile demand for ATP any increase in oxidative metabolism is indicative of a spasminogen being present in the specimen.

An increase in oxidative metabolism above 3 times basal rate should be taken as strongly indicative of a spasminogen being present in the specimen.

In the alternative, the smooth muscle cells of the sample may have a contractile demand for ATP. In which case, one looks for an increase in oxidative metabolism which is not attributable to that contractile demand. This may be done by comparison to a control incubation in which the cells have a contractile demand for ATP, prior to application of the fluid specimen. One may then compare any increases in oxidative metabolism before and after addition of the fluid sample. As an alternative, a test incubation may be compared to a 'separate' control incubation; 'separate' in that it is a different incubation comprising a separate, but comparable model cell or tissue sample, treated/incubated identically except for the addition of the fluid sample.

The present invention also provides a method of treating a patient with sub-arachnoid haemorrhage and at risk of going into chronic vascular vasospasm which comprises administering to the patient: (a) a compound which puts VSM cells into the contracted state and/or (b) a compound which blocks the effects of the spasminogen.

Histamine is an example of a compound which puts VSM cells into the dephosphorylated state following contraction (known as the "latched" state). Vascular smooth muscle contraction requires myosin light chain kinase to phosphorylate Myosin ATPase, and myosin ATPase to interact with actin before it can generate tension. It is unique however, when compared to other muscles because it can maintain tension for extended periods with low energy costs (Dillon, P. F. et al 1981 Science 211, 495–497; Lynch, R. M. and Paul, R. J. 1987 Am.J.Physiol. 256, c328–c334; Hai, C. M. and Murphy, R. A. 1988 Am.J.Physiol. 254, c99–c106). Increased intracellular calcium ($Ca^{++}$) concentration, which stimulates myosin light chain kinase, is needed to generate but not to maintain tension (Dillon, P. F. et al., 1981 supra). Indeed, near maximal tension can be maintained with $Ca^{++}$ concentrations below those necessary to half maximally activate myosin light chain kinase (Hai, C. M. and Murphy, R. A. 1988). This condition is achieved by de-phosphorylating myosin ATPase, when attached to actin, effectively 'locking' the two proteins together. This 'locked together' state is called latch and is insensitive to $Ca^{++}$ stimulation (Hai, C. M. and Murphy, R. A. 1988). Numerous other enzymes however, are sensitive to cytosolic $Ca^{++}$ such as Krebs cycle enzymes (Drummond, R. M. J. V. et al., 1995 Biophysics J. 68, A230) and its is though that calcium activation of the mitochondria may be essential during periods of high metabolic flux.

Putting VSM cells into the "latched" state appears to prevent VSM experiencing an increase in respiratory flux in consequence of contact with the spasminogen.

Dobutamine which also puts VSM cells into the "latched" state, appears to block the effects of the spasminogen.

Therefore the present invention provides treatment methods based on both histamine and dobutamine.

A suitable treatment may comprise use of 500 mg dobutamine in 50 mls normal saline. Infusion commencing to give 1 mg/hour rising to 10–15 mg/hour. Infusion may be continued for a period (generally 24–48 hours) sufficient to give the desired blood pressure response (eg $^{120}/_{90}$) or renal output response.

The present invention also provides use of compounds as set out in (a) and (b) above the histamine and dobutamine, in the preparation of medicaments for the treatment of chronic cerebral vasospasm.

The present invention provides an assembly of a test apparatus and a cell or tissue sample wherein:
the test apparatus comprises a vessel, a lid to render said vessel air-tight and an oxygen sensor for measurement of the oxygen concentration of any solution in said vessel; and
the cell or tissue sample comprises a portion human basilar artery or a sample of vascular smooth muscle cells.

The assembly may comprise a stirring means within the vessel. The assembly may comprise a liquid medium for location in the vessel. Suitable mediums are hereafter described.

The incubation mediums used in the methods and assemblages described above may be free of any material comprising cells which may be undergoing metabolic processes. Thus they may be free of viable microorganism such as bacteria. The mediums may be rendered free of viable microorganisms by use of suitable sterilising techniques, filters (eg filters for removal of bacteria) or other methods known to those skilled in the art.

In using a method as stated above to identify a spasminogen which induces spasm of smooth muscle cells, the present inventors have made the unexpected discovery that okadaic acid stimulates an increase in oxidative metabolism in porcine carotid artery. The effect caused by okadaic acid is very similar to that caused by subarachnoid haemorrhage supernatant. In investigating this further, the inventors have obtained experimental results which indicate that the physical properties of the substance in subarachnoid haemorrhage supernatant which acts as a spasminogen appear to be consistent with those of okadaic acid. Specifically both are acid stable, they both have hydrophilic and hydrophobic domains, they both have a molecular weight of less than 1000 daltons. Okadaic acid has a molecular weight of 805 daltons, it is lipophilic, protein philic (but not a protein itself).

Okadaic acid is a lipophilic compound which is a phosphatase-specific inhibitor. It is known to cause smooth muscle constriction. It was originally found in molluscs. Inhibition of the de-phosphorylation of myosin ATPase would cause an increased ATPase activity (see earlier in this text).

The present inventors therefore suggest that: (i) the pathophysiological mechanism for chronic vasospasm/vasoconstriction is likely to involve phosphatase inhibition or loss of kinase and/or ATPase control; and (ii) the spasminogen is likely to comprise a molecular entity which brings about phosphatase inhibition. Alternatively the spasminogen may be a molecular entity which brings about activation of a protein kinase. The result of inhibition of protein phosphatase activity is an increase in the population of phosphorylated proteins. This is also the result when protein kinases (eg protein kinase C "PKC") are activated. Indeed, phorbol esters such as phorbol-meristate will cause a significant activation of PKC in vascular smooth muscle (and other tissues). In vessels, PKC activation results in the phosphorylation of Calponin and Caldesmon. These proteins are inhibitory proteins of myosin ATPase and when phosphorylated their inhibition of myosin ATPase is removed. Therefore, by active phosphorylation of Calponin and Caldesmon myosin ATPase is no longer inhibited, resulting in increased activity; similar to the observations described herein.

Thus the spasminogen may be a molecular entity which is itself a phosphatase inhibitor or an activator of a protein kinase. Alternatively it may be a molecular entity which switches on a phosphatase inhibitor or which stimulates the production of a phosphatase inhibitor. It is also possible that the spasminogenic effect is brought about by a group of compounds which in concert, act to inhibit a phosphatase or activate a protein kinase. Thus the molecular entity which brings about inhibition of phosphatase may be acid stable, with hydrophobic and hydrophilic domains and a mw of less than 1000 daltons. Thus the inventors provide that the spasminogen is a molecular entity (or group of compounds) which brings about phosphatase inhibition or activation of a protein kinase. The molecular entity which switches on a phosphatase inhibitor or which stimulates the production of a phosphatase inhibitor. The spasminogen may comprise a group of compounds which in concert, act to inhibit a phosphatase. The molecular entity or one or more of said group of compounds may be acid stable, with hydrophobic and hydrophilic domains and a mw of less than 1000 daltons. The molecular entity or one or more of said group of compounds may be an okadaic acid-like compound. Thus there is also provided a further new way of diagnosing patients likely to suffer a pathological condition which is in consequence of spasm of smooth muscle cells (such as chronic cerebral vasospasm following from subarachnoid haemorrhage) which comprises obtaining a tissue or fluid sample from a patient and analysing that sample for an inhibitor of a phosphatase or an activator of a protein kinase. The analysis may be for a phosphatase inhibitor which has one or more of the features following: (a) acid stability; (b) mw of less than 1000 daltons; (c) hydrophilic and hydrophobic domains; (d) lipophilic domain; (e) protein philic domain. The analysis may be for a phosphatase inhibitor which inhibits the de-phosphorylation of myosin ATPase. The analysis may be for a compound related to/similar to okadaic acid. One may analyse for an inhibitor of a phosphatase in accordance with techniques which are known and available in the art.

The OxBox and methods as described earlier which measure a marker of oxidative metabolism are sensitive, reliable and quantitative Therefore they may be used as a more general test to aid in diagnosis of and screen for tests involving phosphatase inhibition.

Further provided is the use of a phosphatase inhibitor or protein kinase activator (eg as set out above) to screen for compounds useful as drugs to counter or block their spasminogenic effects on smooth muscle. For example in the screening method described earlier herein, the spasminogenic compound of the incubation may comprise a phosphatase inhibitor such as okadaic acid.

Further provided are treatment methods and medicaments for conditions associated with chronic spasm constriction eg vasospasm/vasoconstriction which are based on the use of a compound which blocks the inhibitory effects of the spasminogen/spasminogenic group of compounds. Thus the treatment compound may block the inhibitory effects of a phosphatase inhibitor, or it may block the switching on of a phosphatase inhibitor, or the production of a phosphatase inhibitor. Such a compound may comprise a specific binding partner for the phosphatase inhibitor. Where this is so, the specific binding partner would in essence be "mopping-up" the inhibitor, thereby reducing or preventing its normal interaction with the phosphatase.

In relation to the above, a specific binding partner comprises a member of a specific binding pair which have particular specificity for one another and which in normal conditions bind to each other in preference to other molecules. Examples of specific binding pairs are antigens and antibodies (eg in the example stated above the phosphatase inhibitor would be the antigen in the context of an immuno-based specific binding pair); ligands and receptors; ligands and enzymes; enzymes and substrates; and complementary nucleotide sequences. The skilled person will be able to think of many other examples and there is no need to list them all here. Further the term "specific binding pair" is also applicable where either or both of the constitutive elements comprise part of a larger molecule.

Alternatively, the compound may comprise a different non-functional (in the sense of not inhibiting the normal catalytic action of the phosphatase) ligand for the phosphatase ie a mimic ("mimetic") of the inhibitor. Where this is so, the phosphatase binding sites available for interaction with the inhibitor are effectively reduced, thereby leading to a reduction in the inhibitory effects of the ligand.

The designing of mimetics and structural analogues (such as antagonistic structural analogues) is a known approach to the development of pharmaceuticals based on a lead compound.

In order that the present invention is clearly understood, embodiments and examples will now be described by way of illustration only with reference to the figures referred to below.

The examples and embodiments described herein serve to illustrate the present invention and are not to be interpreted as limiting its scope.

Figure 1:
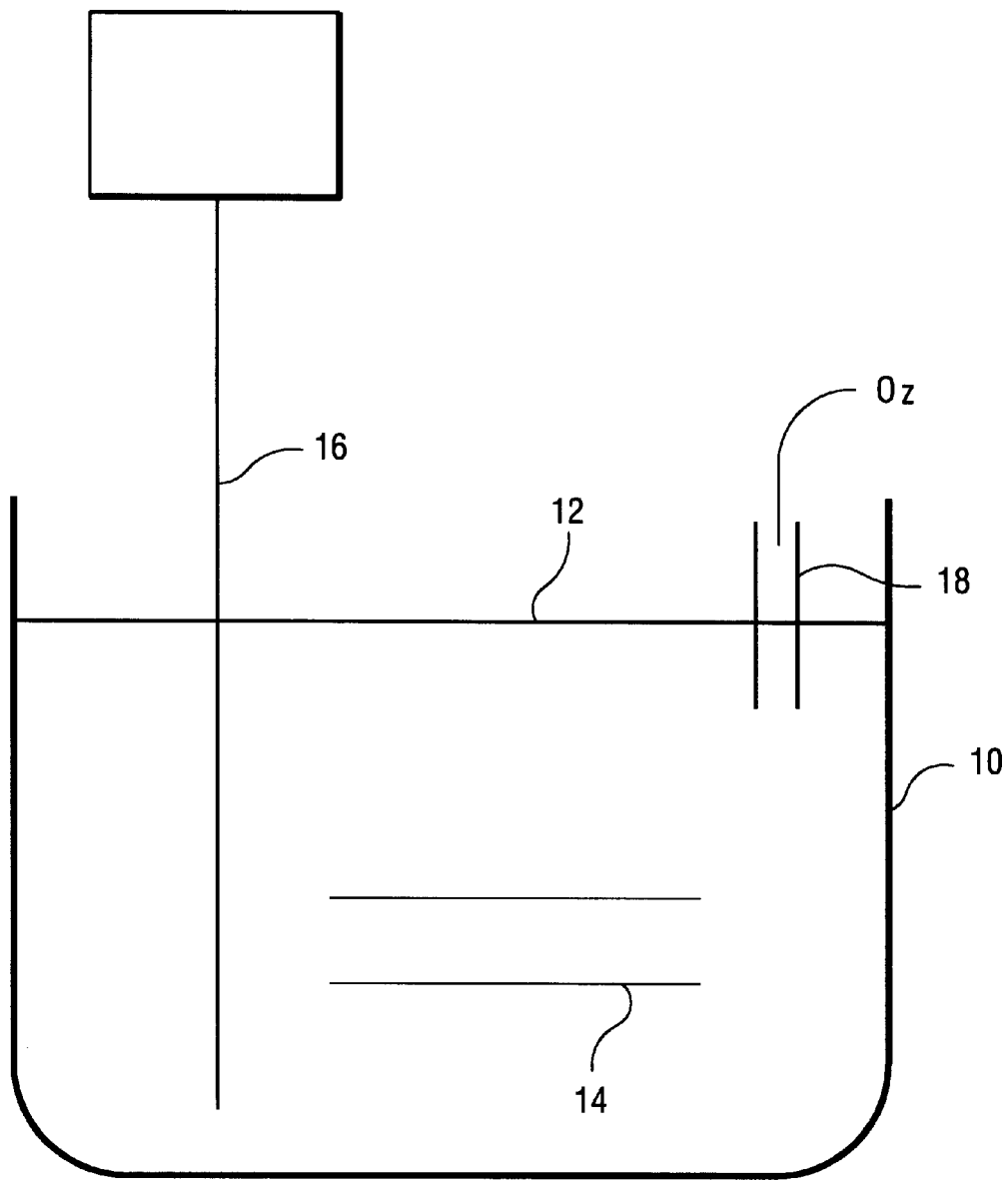
FIG. 1 is a simple diagrammatic representation of the measurement device (hereafter called a "OxBox").

Oxygen consumption of a tissue or cell sample can be measured by use of a simple device as represented in FIG. 1 and which the inventors call an OxBox.

A sample of tissue comprising muscle cells such as porcine carotid artery (14) is dissected out at 4° C. from source eg a recently killed pig and the surrounding tissues removed. The tissue sample is maintained at 30° C. in an airtight vessel (10) in a previously aerated (18) solution (12) for supporting oxidative metabolism. The vessel (10) should be heat and light resistant and it may be made of any material providing such qualities eg glass, perspex, plastic. Other materials will be known to those skilled in the art.

Any tissue appropriate to the type of vasospasm under study may be used. For example if one is concerned with the diagnosis of cerebral vasospasm, porcine carotid tissue or basilar artery tissue may be used. If one is diagnosing cardiac vasospasm, suitable coronary artery tissue may be selected. Alternatively, one may use a culture of suitable muscle cells. Species and vascular bed cross-over is perfectly possible and exemplified.

A suitable solution (12) for maintenance of the tissue sample and oxidative metabolism is Krebs buffer with 11 mM glucose and/or 5 mM pyruvate. An alternative solution is Hepes. Others appropriate to the maintenance of the tissue or cells being used will be known to those skilled in the art. The pH should be around 7.4.

An oxygen sensor (16) is suspended in the solution for the measurement of oxygen consumption over suitable period of time (eg 1 to 5 hours) under varied experimental conditions.

EXAMPLE 1

An approximately 0.5 g sample of porcine carotid artery is used in an OxBox as generally described above. The sample is immersed in 6 ml of buffer solution, exposed to air (approx. 20% oxygen) with a resting oxygen consumption rate of 0.2 μMol/mg wet weight tissue/min. The tissue sample is maintained in these conditions for 30 mins, and the oxygen concentration in the chamber measured over a period of time to give the tissue's basal rate of oxygen consumption in non-working conditions.

A 200 μls sample of either sub-arachnoid haemorrhage CSF supernatant (A) or peripheral blood serum (B) (blood collected in a collection tube comprising a suitable coagulant such a sodium citrate; the serum produced by spinning down the blood or supernatant at 1000 rpm for 20 min.; it its preferable to avoid use of heparin as the anticoagulant as it can upset intracellular signalling mechanisms) from a patient in chronic cerebral vasospasm is added to the vessel and the oxygen concentration measured over a period of 300 minutes in order to determine any change in the rate of oxygen consumption.

Suitable controls (C) are set up. These controls may simply be without sample. Alternatively, they may comprise biological samples known not to contain a spasminogen eg human serum or CSF from a patient with hydrocephalus, but not in vasospasm. Otherwise identical experimental conditions are used.

Figure 2:
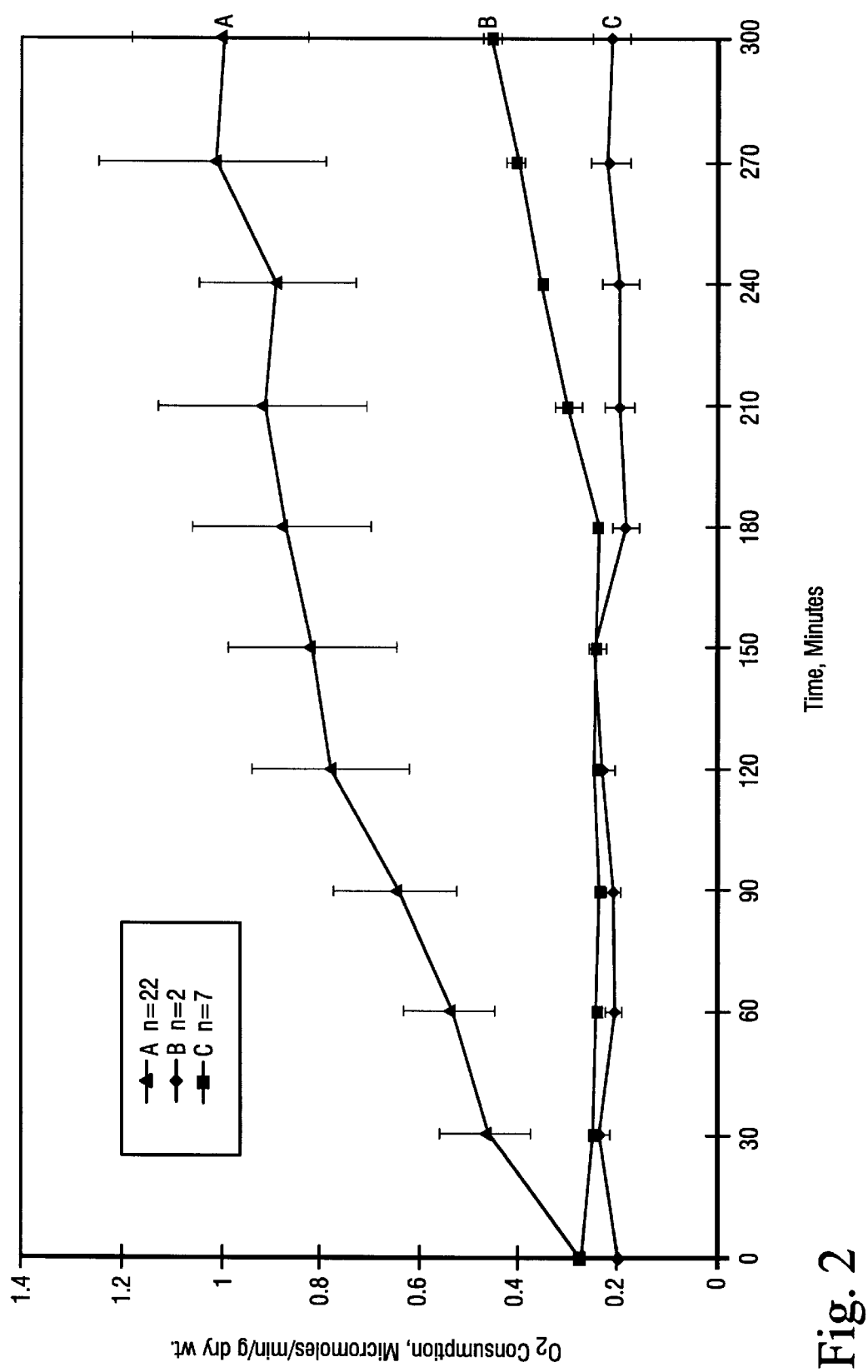
FIG. 2 shows the effect of blood or sub-arachnoid CSF supernatant from a patient with chronic cerebral vasospasm on oxygen consumption (micromoles/min/g dry weight) of porcine carotid artery over a period of 5 hours; A=sample of sub-arachnoid haemorrhage supernatant; B=peripheral blood sample; C=control sample.

As can be seen from FIG. 2, a 5x increase in the rate of oxygen consumption is observed for sub-arachnoid haemorrhage supernatant (A). This comprises a first demonstration of a vasoactive compound in CSF. Peripheral blood (B) from such a patient, although causing a definite and consistent increase in the rate of oxygen consumption, does not produce an effect as marked as sub-arachnoid haemorrhage supernatant. Controls (C) as discussed above, do not have an effect on oxygen consumption.

EXAMPLE 2

Figure 3:
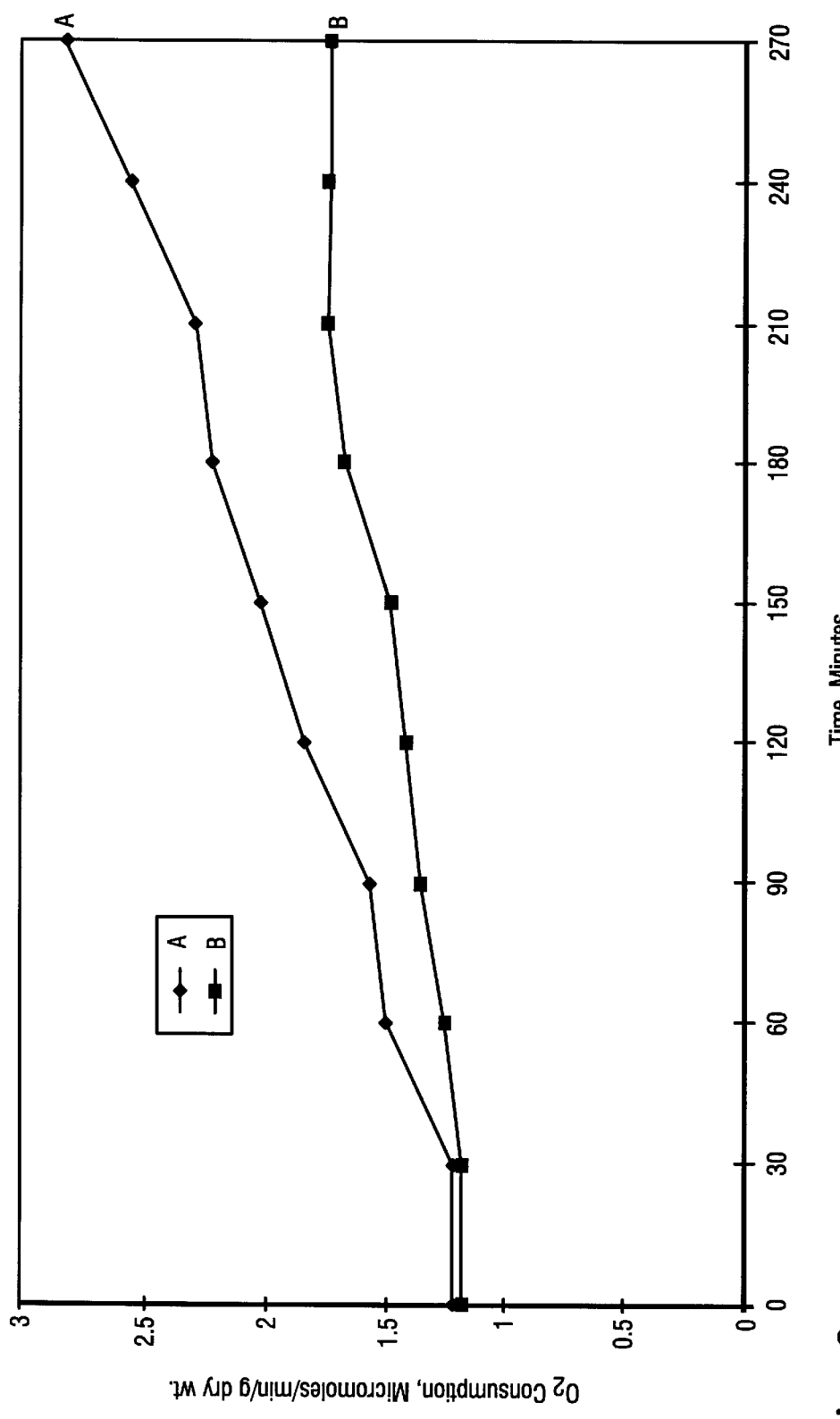
FIG. 3 shows the effect of blood or sub-arachnoid CSF supernatant from a patient with chronic cerebral vasospasm on oxygen consumption (micromoles/min/g dry weight) of rat aorta over a period of 4.5 hours; A=sample of sub-arachnoid haemorrhage supernatant; B=peripheral blood sample.

The experiment is conducted as for Example 1, except that rat aorta is used instead of porcine carotid artery. The test samples are (A) and (B) as above. The results are shown in FIG. 3. As in Example 1 above, a 5x increase in the rate of oxygen consumption is observed for sub-arachnoid haemorrhage supernatant (A) and the increase in oxygen consumption associated with peripheral blood (B) is not so marked. The experiment shows that the results shown in FIG. 2 are not specific to porcine carotid artery.

EXAMPLE 3

The experiment is conducted as for Example 1, except that this time peripheral blood from a sub-arachnoid haemorrhage patient with chronic cerebral vasospasm (B) is compared with peripheral blood from a patient not in chronic cerebral vasospasm (C).

Figure 4:
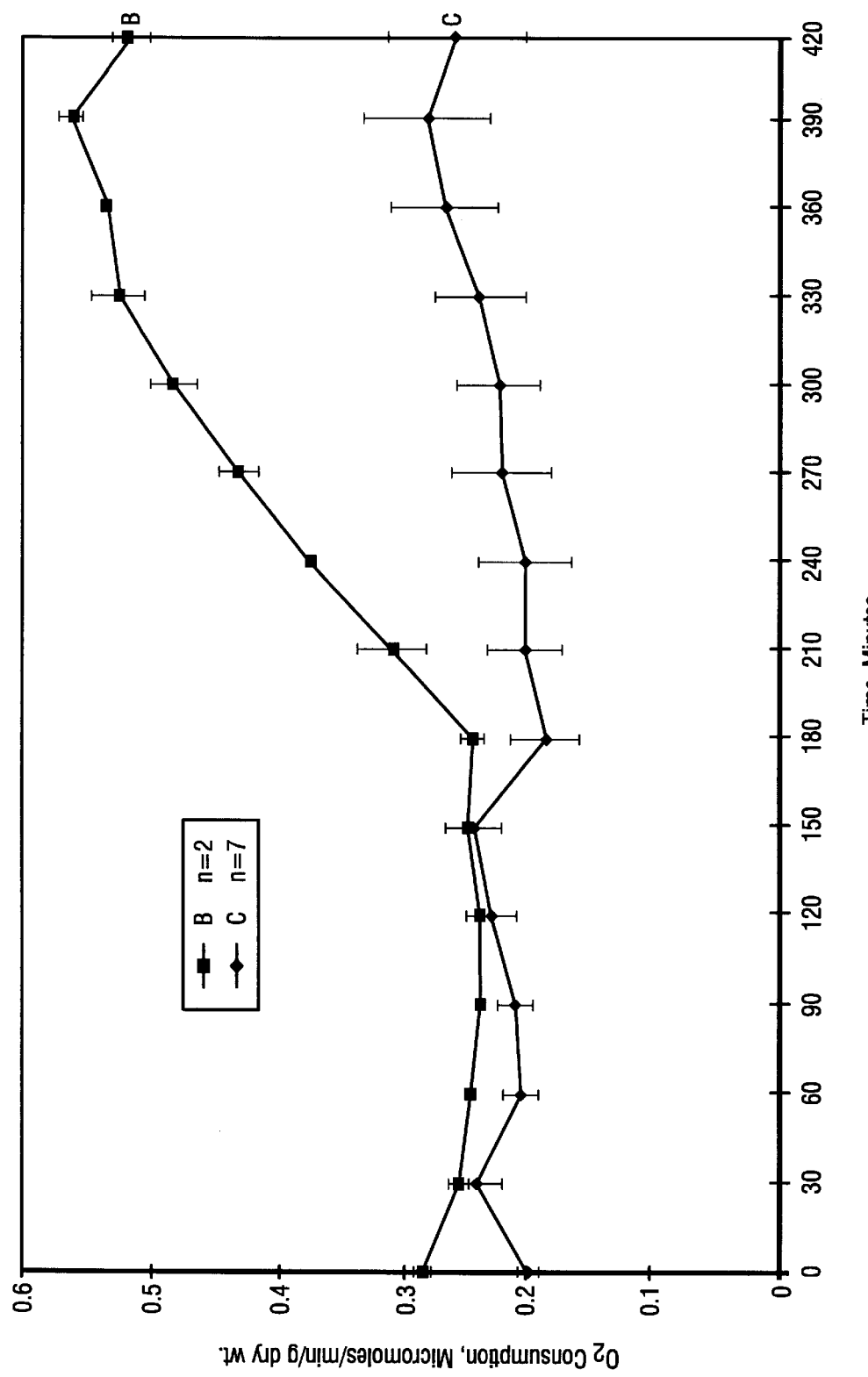
FIG. 4 compares the effect of blood from a patient with chronic cerebral vasospasm (B) with blood from a patient not having chronic cerebral vasospasm (C) on oxygen consumption (micromoles/min/g dry weight) of porcine carotid artery over a period of 7 hours.

As can be seen from FIG. 4, peripheral blood from a patient in chronic vasospasm causes about a 2x increase in oxygen consumption, whereas peripheral blood from the control patient showed only a very small increase of no significance. In order to better observe the effects on oxygen consumption caused by peripheral blood from a patient in chronic cerebral vasospasm, it is advantageous to increase the incubation time. This can be seen from a comparison of FIGS. 2 and 4.

EXAMPLE 4

Figure 5:
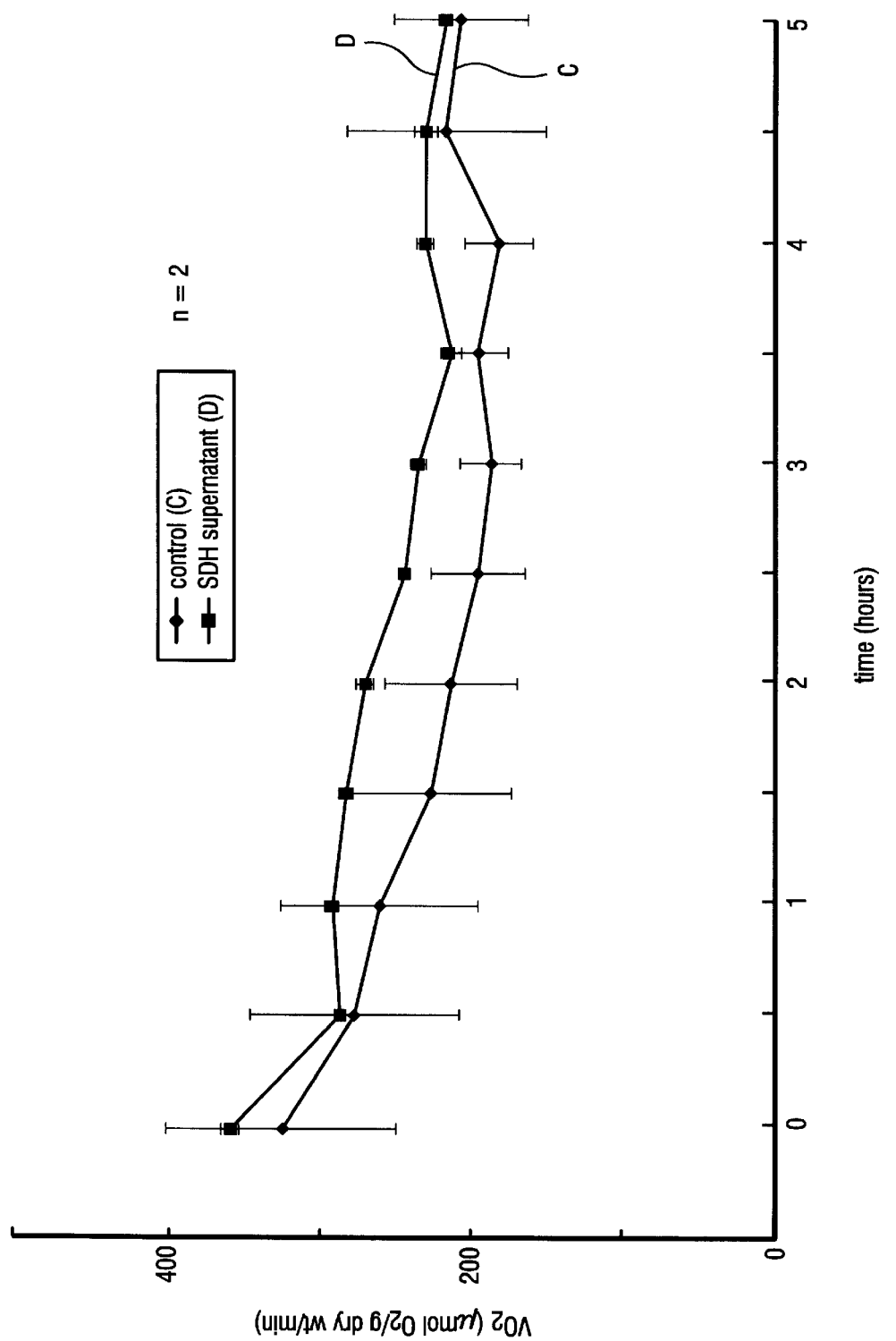
FIG. 5 shows the effect of sub-dual haemorrhage supernatant on oxygen consumption (micromoles/min/g dry weight) or porcine carotid artery over a period of 5 hours; C=control sample; D=supernatant from the sub-dural space.
Figure 6:
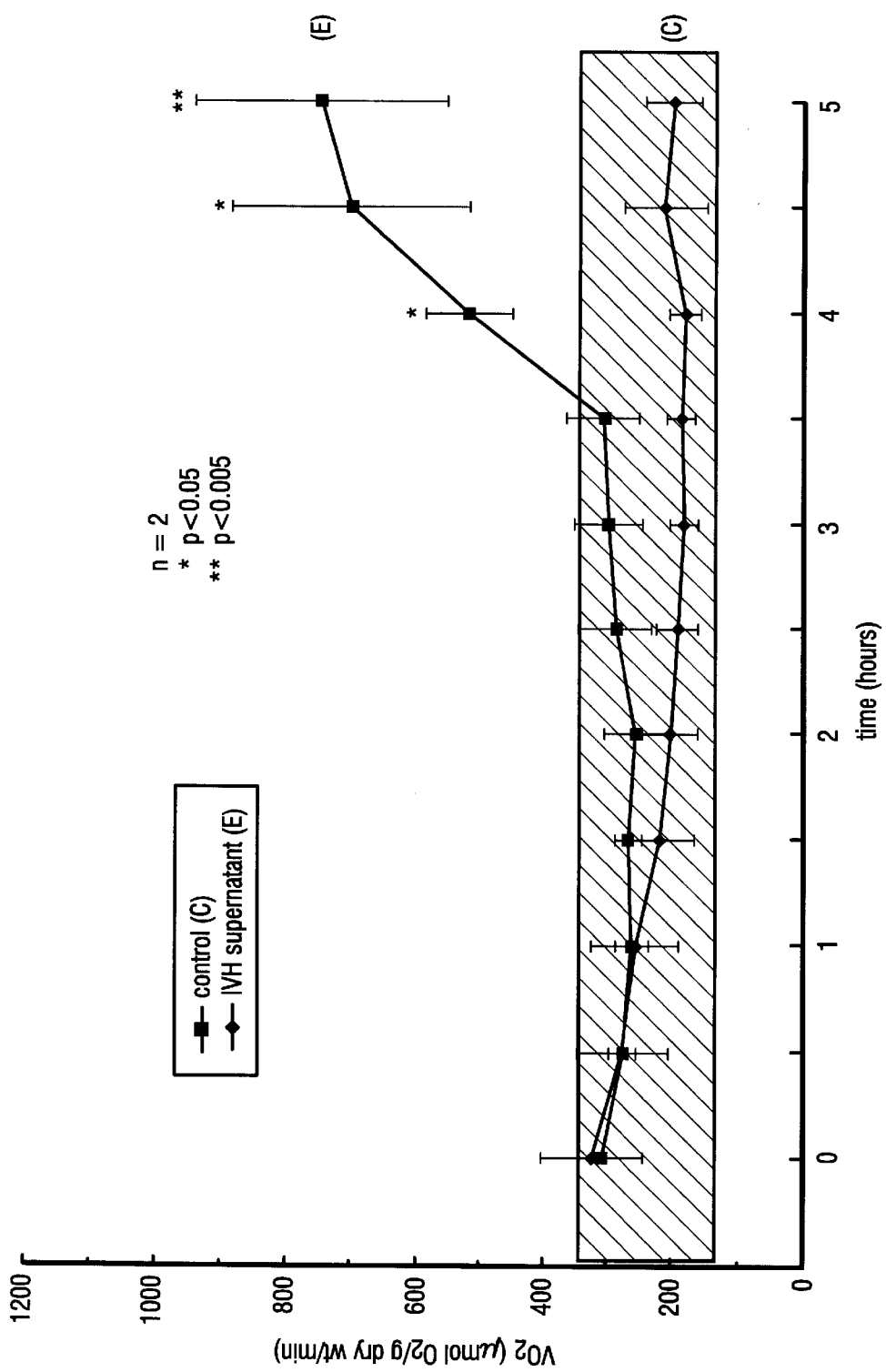
FIG. 6 shows the effect of intraventricular haemorrhage supernatant on oxygen consumption (micromoles/min/g dry weight) of porcine carotid artery over a period of 5 hours; C=control sample; E=intraventricular haemorrhage supernatant.

The experiment is conducted as for Example 1, except that this time the test samples comprise either supernatant haemorrhage (E) of a patient with chronic cerebral vasospasm following intraventricular haemorrhage. As can be seen from FIG. 5, supernatant from the sub-dural space does not increase oxygen consumption. FIG. 6 shows that intraventricular haemorrhage supernatant although causing an increase in oxygen consumption, has an attenuated effect in that it takes about 3.5 hours for the increase in oxygen consumption to start. As can be seen from FIG. 2, supernatant from the sub-arachnoid space of a patient in chronic cerebral vasospasm, causes an almost immediate increase in the rate of oxygen consumption. This result suggest that in sub-arachnoid haemorrhage vasospasm the spasminogen may be associated with the mixing of blood and CSF of the sub-arachnoid space.

EXAMPLE 5

Figure 7:
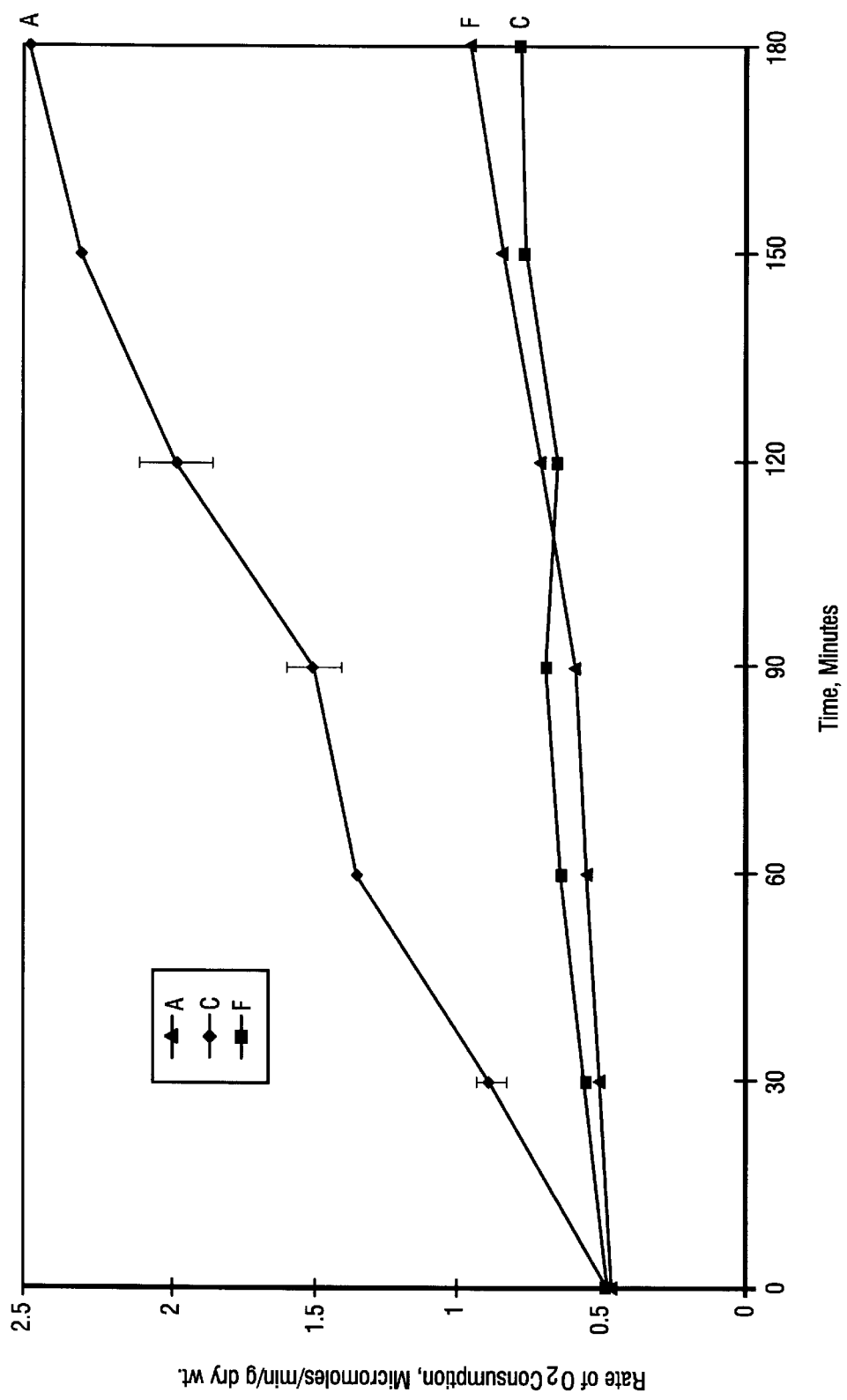
FIG. 7 shows the effect of histamine and sub-arachnoid haemorrhage supernatant on the oxygen consumption (micromoles/min/g dry weight) of human basilar artery over a period of 3 hours; A=sample of sub-arachnoid haemorrhage supernatant; F=pretreatment with histamine; C=control sample.

The experiment is conducted as for Example 1, except that human basilar artery is used instead of porcine carotid artery. The experiment investigates the effects of histamine pre-treatment. If the artery is pre-treated with histamine (F) (histamine concentration of $10^{-4}$ molar in the 6 mls of OxBox buffer for 1 hour) the large increase in oxygen consumption in response to supernatant from the sub-arachnoid space of a patient in chronic vasospasm (a) was abolished. The effect is shown in FIG. 7.

EXAMPLE 6

Porcine carotid arteries are maintained in ice cold physiological salie solution (PSS) containing (in mM) 116 NaCl, 25 NaHC03, 5.4 KCL, 5 KH2PO4, 1.2 CaCl2, 1.25 MgSO4 and 11 glucose. The arteries are debrided of fat and connective tissue at 4° C. 2–3 g wet weight of arteries are placed in a 10 mm diameter NMR tube and superfused at 37° C. at a constant flow rate of 20 ml/min with Krebs-Hensleit buffer containing 0.5 mM KH2PO4 with either 11 mM glucose or 5 mM pyruvate as the substrate and aerated with 95%O2–5%CO2. The arteries were perfused for 90 min in control media and then in the presence of Krebs-Hensleit buffer supplemented with 1 part to 30 sub-arachnoid haemorrhage supernatant collected from four patients with angiographic vasospasm. The carotids are equilibrated for 20 minutes in the NMR tube and the ATPase flux measured in a 400 MHz magnet interfaced to a Bruker spectrometer.

ATPase flux (ATP to ADP) increases 6 fold (0.02–0.12 μmol/g/s) and is sustained for 18 hrs. Adenylate kinase (Pi+ADP to ATP) fails to keep pace with ATPase flux and therefore ADP levels increase (41 to 114 μmol/L).

Therefore haemorrhagic CSF caused a large and sustained increase in ATPase activity; far more than any known spasminogens or vasoconstrictors. The haemorrhagic CSF appears to directly stimulate actinomysin ATPase in smooth muscle. The mitochondria respond, but are unable to maintain metabolic homeostasis and ADP increases.

EXAMPLE 7

The OxBox as described herein can be used to monitor the treatment of chronic cerebral vasospasm or other such conditions such as cardiac vasospasm. The present example concerns monitoring treatment of chronic cerebral vasospasm with dobutamine. 1 day following the onset of sub-arachnoid haemorrhage, a blood or CSF sample from a patient is diagnosed as being able to stimulate eg porcine carotid artery to increase oxygen consumption and therefore as comprising a spasminogen (see Example 1) Such a sample is described as being "hot". The patient is started on a suitable vasoactive agent such as dobutamine eg 500 mg dobutamine in 50 mls normal saline. Infusion commencing at 2.5 µg/kg body weight/min. rising to 10 µg/kg body weight/min. Infusion may be continued for up to 10 days. (Dobutamine is conventionally used in the treatment of renal failure and high blood pressure). The patient is monitored by use of the Ox-Box on eg days 2, 4 and 8, until the sample withdrawn from the patient turns "cold" ie no longer able to stimulate porcine carotid artery to increase oxygen consumption.

Typically the sample will turn cold within hours of dobutamine infusion indicating the effectiveness of treatment with dobutamine.

EXAMPLE 8

The OxBox as described herein can be used to screen for new drugs to treat conditions such as chronic cerebral vasospasm which result form spasm of smooth muscle cells. As shown in Example 5 pretreatment of human basilar artery tissue with histamine reduces the rate of oxygen consumption to near that of the control upon application of sub-arachnoid haemorrhage supernatant (FIG. 7), when measured over a period of 180 minutes. Histamine is known to put vessels into a contracted state and the present inventors believe that this contracted state may protect the stimulation of ATPase caused by the supernatant.

Thus the OxBox and method as described herein can be used to look for drugs which block the spasminogenic effects of the CSF. The results shown in FIG. 7 indicate the effectiveness of histamine as a treatment to prevent chronic cerebral vasospasm.

EXAMPLE 9

Figure 8:
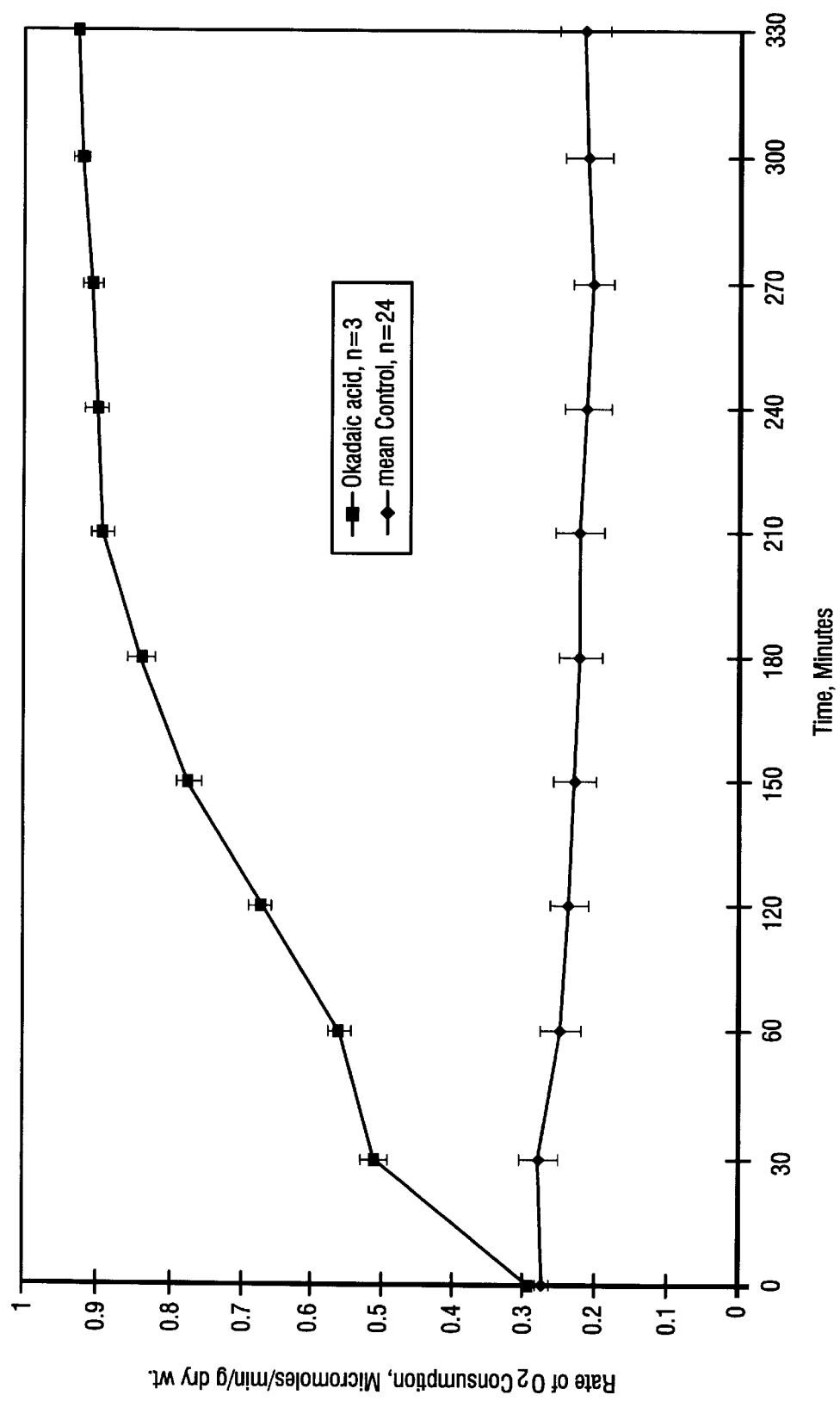
FIG. 8 shows the effect of okadaic acid on oxygen consumption (micromoles/min/g dry weight) of porcine carotid artery over a period of a period of about 5 hours.
Figure 9:
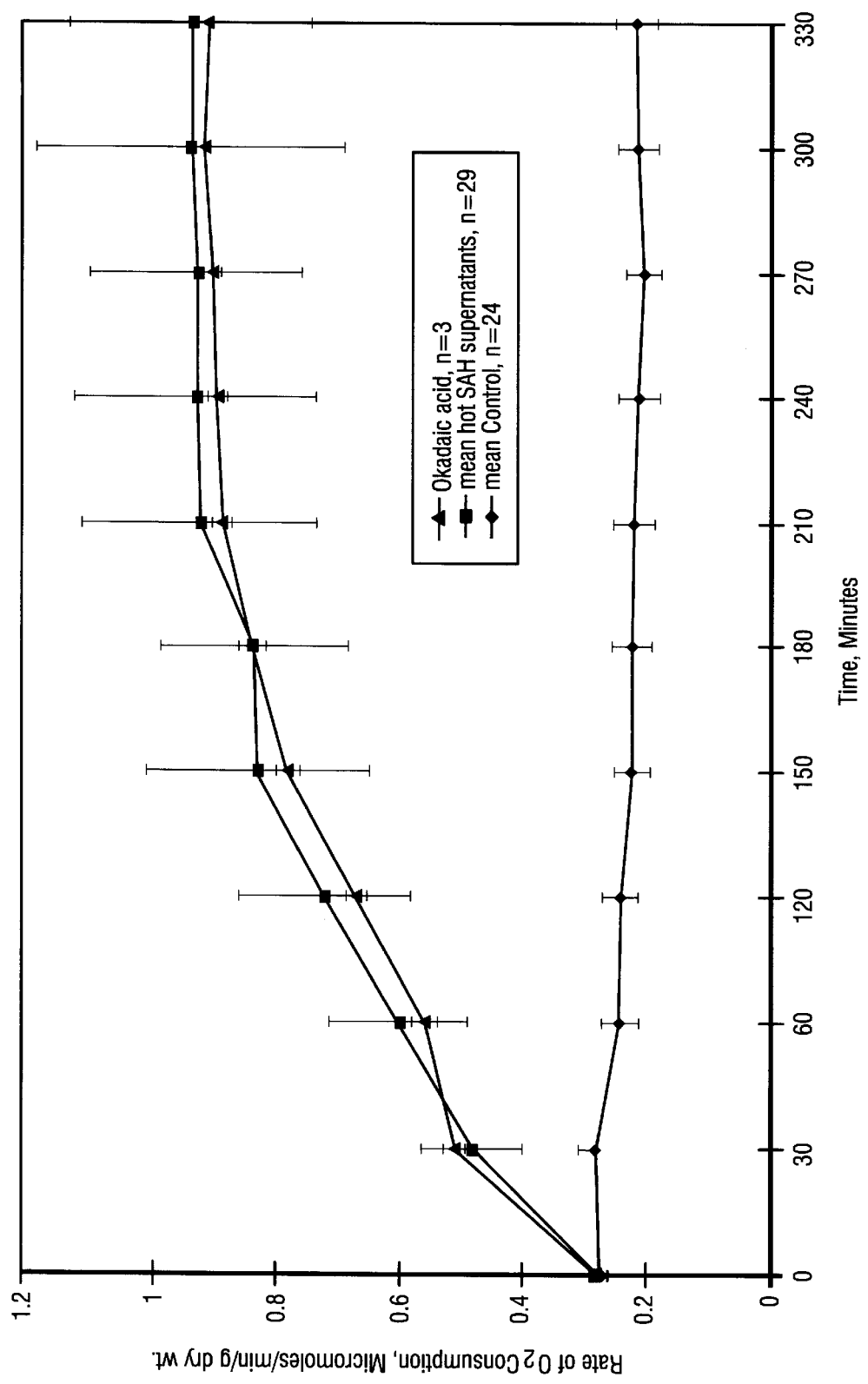
FIG. 9 shows the closely comparable effects of okadaic acid and sub-arachnoid CSF supernatant from a patient with chronic cerebral vasospasm on oxygen consumption (micromoles/min/g dry weight) over a period of about 5 hours.

The OxBox as described herein can be employed in the elucidation of spasminogens. Suspected spasminogens can be tested for increasing oxygen consumption of eg porcine carotid artery as described in Example 1. In one such test, porcine carotid artery was stimulated with 1 nm okadaic acid and the oxygen consumption rate measured over a period of about 5 hours. The results are shown in FIGS. 8 and 9. It can be seen that okadaic acid causes an increase in oxygen consumption strikingly similar to that caused by sub-arachnoid CSF supernatant from a patient with chronic cerebral vasospasm.

EXAMPLE 10

The experiment is conducted as for Example 1, except that this time the effects of sera obtained from pre-eclampsic patients is compared with sera taken from normal pregnant and non-pregnant controls. The data (see FIGS. 10 and 11) shows that metabolic changes in vessels exposed to sera from pre-eclampsia patients are comparable to the metabolic changes in vessels exposed to eg CSF from patients with sub-arachnoid haemorrhage vasospasm or okadaic acid an inhibitor of phosphatase type 2A.

Figure 10:
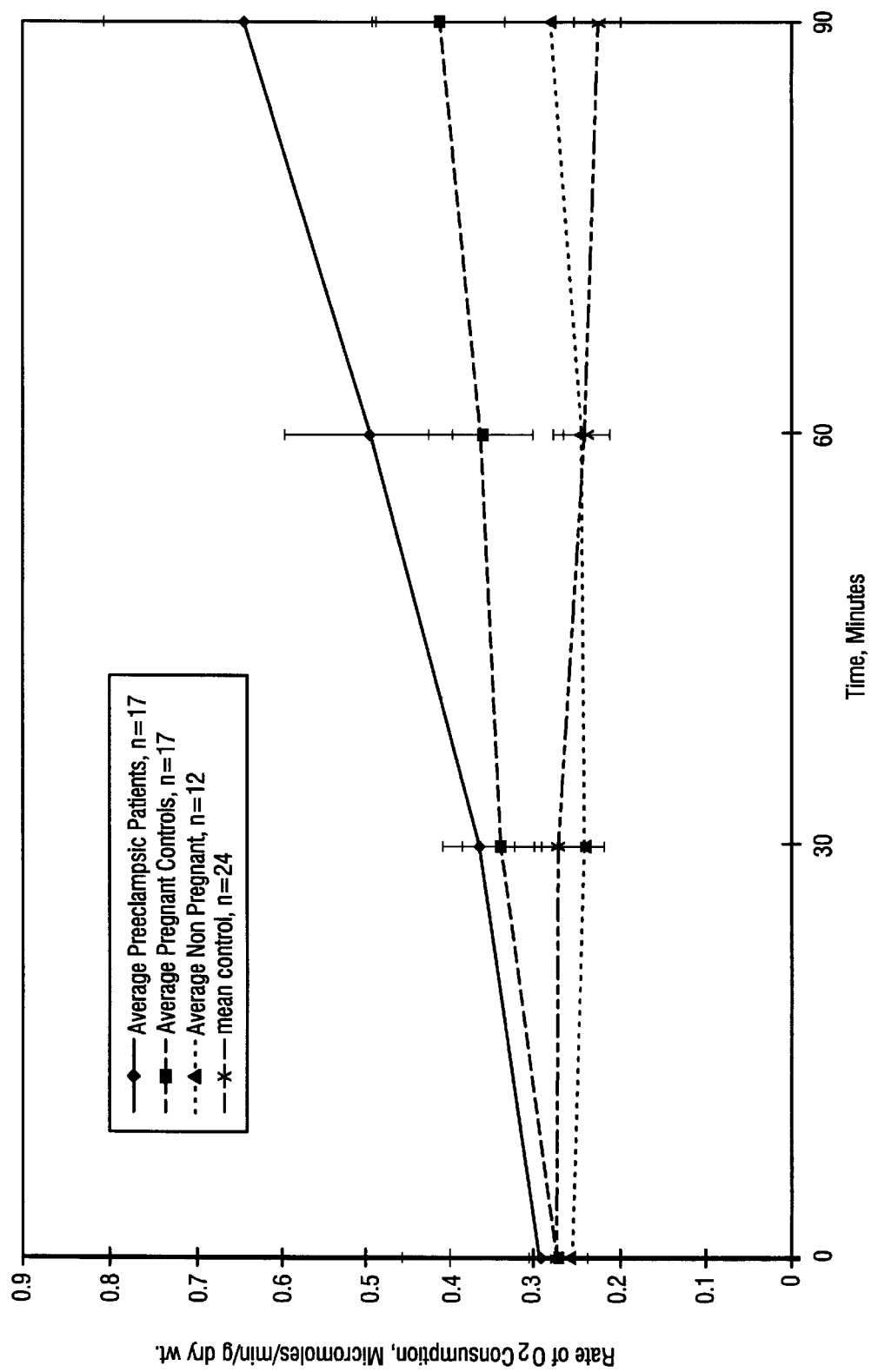
FIG. 10 shows rate of oxygen consumption (micromoles/min/g dry weight) by porcine carotid arteries in the presence of blood plasma from pre-eclamptic, normal pregnant and non-pregnant women and in the absence of plasma.

In pre-eclampsia patients, there was a significant stimulation of respiration after 90 minutes when the porcine carotid arteries were exposed to the serum of pre-eclampsia patients (when compared to matched controls; FIG. 10; n=17 matched pairs). Frequently a five fold increase in oxygen consumption was seen in resting (non-contracting) porcine carotid artery in response to serum from pre-eclampsia patients.

Figure 11:
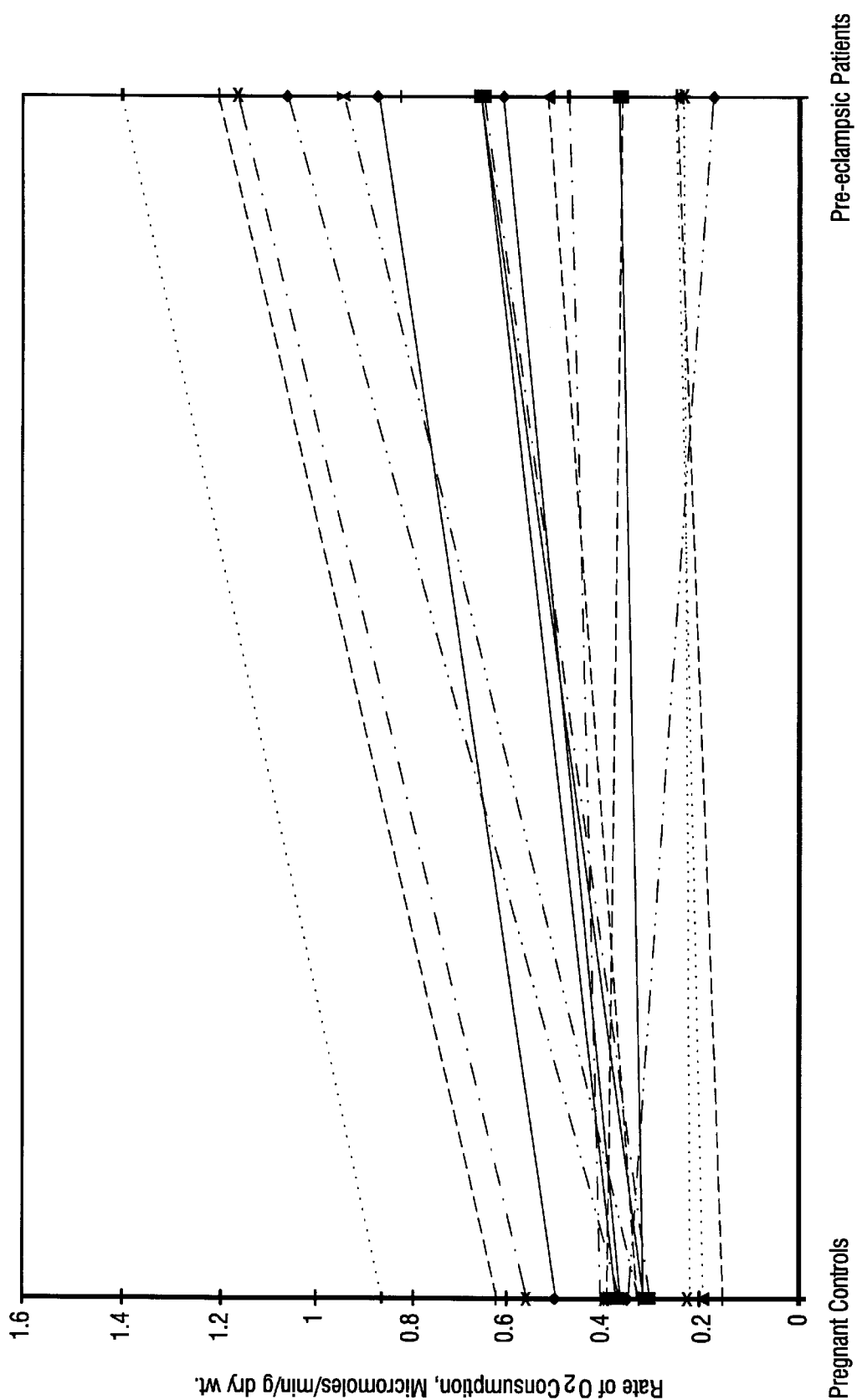
FIG. 11 shown individual rates of oxygen consumption (micromoles/min/g dry weight) at 90 minutes by porcine carotid arteries in the presence of blood sera from pre-eclampsic patients and their matched pregnant controls.

Moreover, in a comparison of pre-eclampsic and pregnant control sera there is a striking acceleration of respiration, which is significantly greater than control FIG. 11). All experiments were performed at 30° C. on resting, non-contracting vessels.

Interestingly, the spasminogens causing cerebral vasospasm stimulating vessels during pre-eclampsia may not be the same. Two differences point to this. Firstly, the pre-eclampsia stimulation is completely reversible by eg rinsing, whilst cerebral vasospasm stimulation is not. Secondly, the stimulation could be prevented if the cerebral vasospasm CSF was pre-treated with esterase. In contrast esterase treatment had no effect on pre-eclampsic sera's stimulation of the vessels.

EXAMPLE 11

The experiment is conducted as for Example 1, except that this time the effects of CSF obtained from Alzheimer's Disease patients is compared with CSF from individuals without the disease. The data (see FIGS. 12, 13 and 14) shows that metabolic changes in vessels exposed to CSF from Alzheimer's Disease patients are comparable to the metabolic changes in vessels exposed to eg CSF from patients with sub-arachnoid haemorrhage vasospasm or okadaic acid an inhibitor of phosphatase type 2A/

Figure 12:
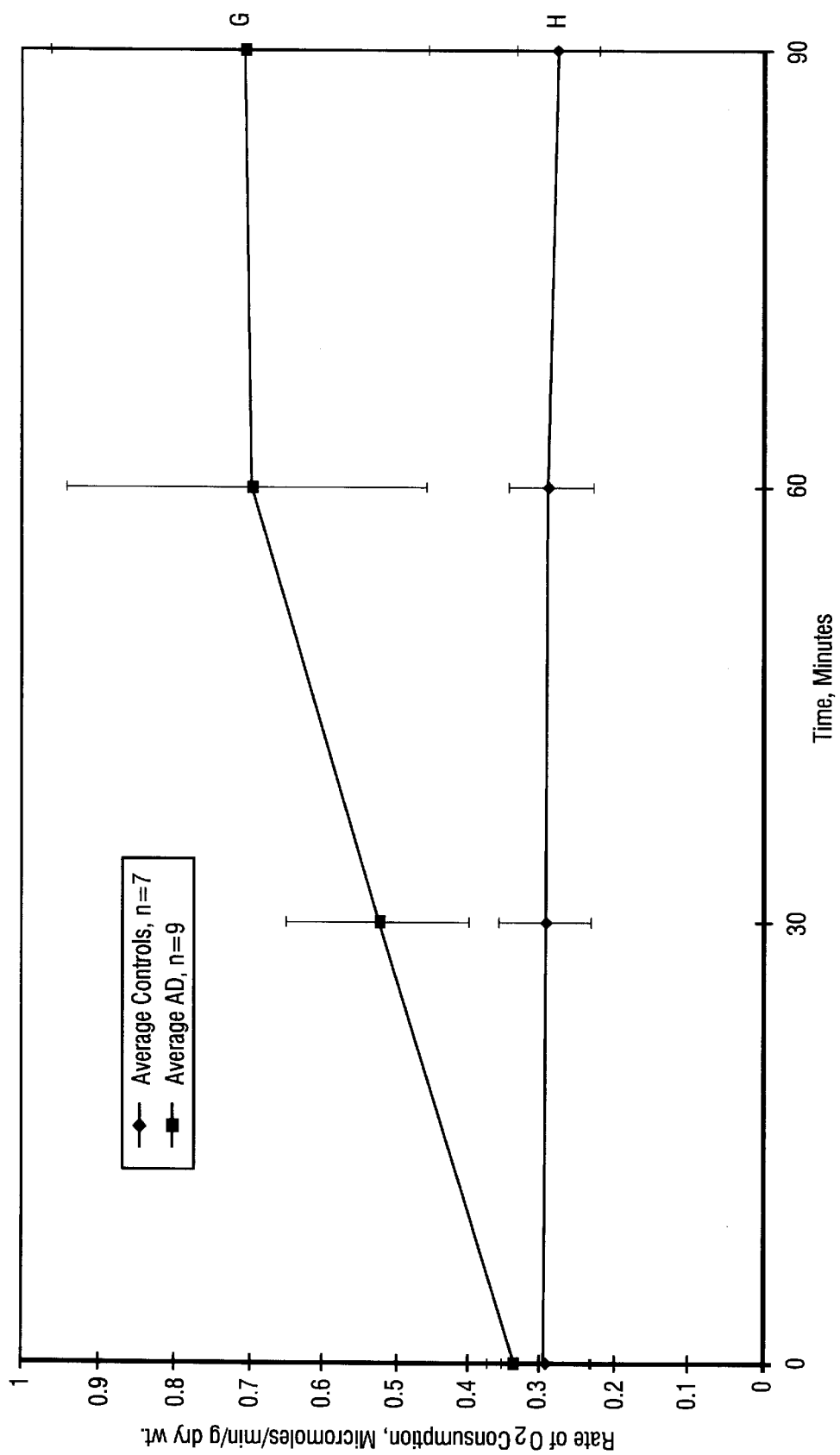
FIG. 12 shows the shows rate of oxygen consumption (micromoles/min/g dry weight) by porcine carotid arteries in the presence of CSF from patients with Alzheimer's disease.

There was a significant stimulation of respiration after 60 minutes. FIG. 12 shows the rate of oxygen consumption for porcine carotid arteries contacted with CSF from patients with clinically diagnosed Alzheimer's disease (G) and patients without Alzheimer's disease (H). CSF was taken from both groups at the time of post-mortem examination. CSF was added to the standard respiration solution bathing a sample of porcine carotid artery (see earlier). As in Example 1, 1 part (eg 200 µls) CSF was added to 30 parts (6 mls) of respiration solution and the rate of respiration measured for at least 90 minutes. As can be seen from FIG. 12, CSF from Alzheimer's disease is associated with an immediate and significant increase in respiration. CSF from control patients had no such effect. Error bars are standard deviation.

Figure 13:
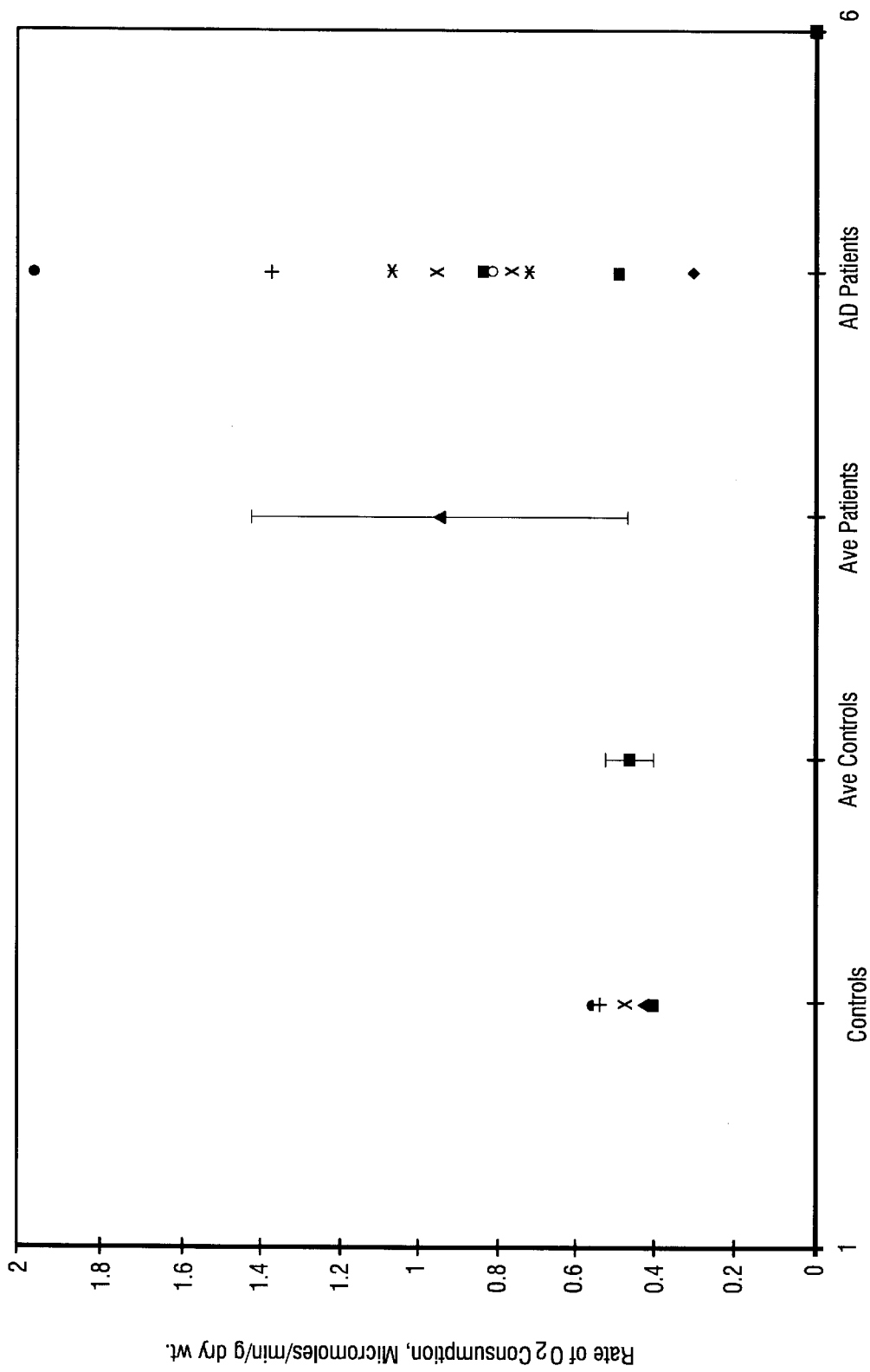
FIG. 13 is a representation of the steady state rate of oxygen consumption (micromoles/min/g dry weight) by porcine carotid arteries in the presence of CSF from patients with Alzheimer's disease and control patients.

FIG. 13 is a graphical representation of the steady state rate of oxygen consumption (ie the rate plotted are those taken at the time when the rate of oxygen consumption had plateaued) in an OxBox system for CSF from Alzheimer's Disease and control patients. As can be seen, CSF from most Alzheimer's Disease patients caused a steady state respiration rate significantly higher than caused by CSF from normal patients.

Figure 14:
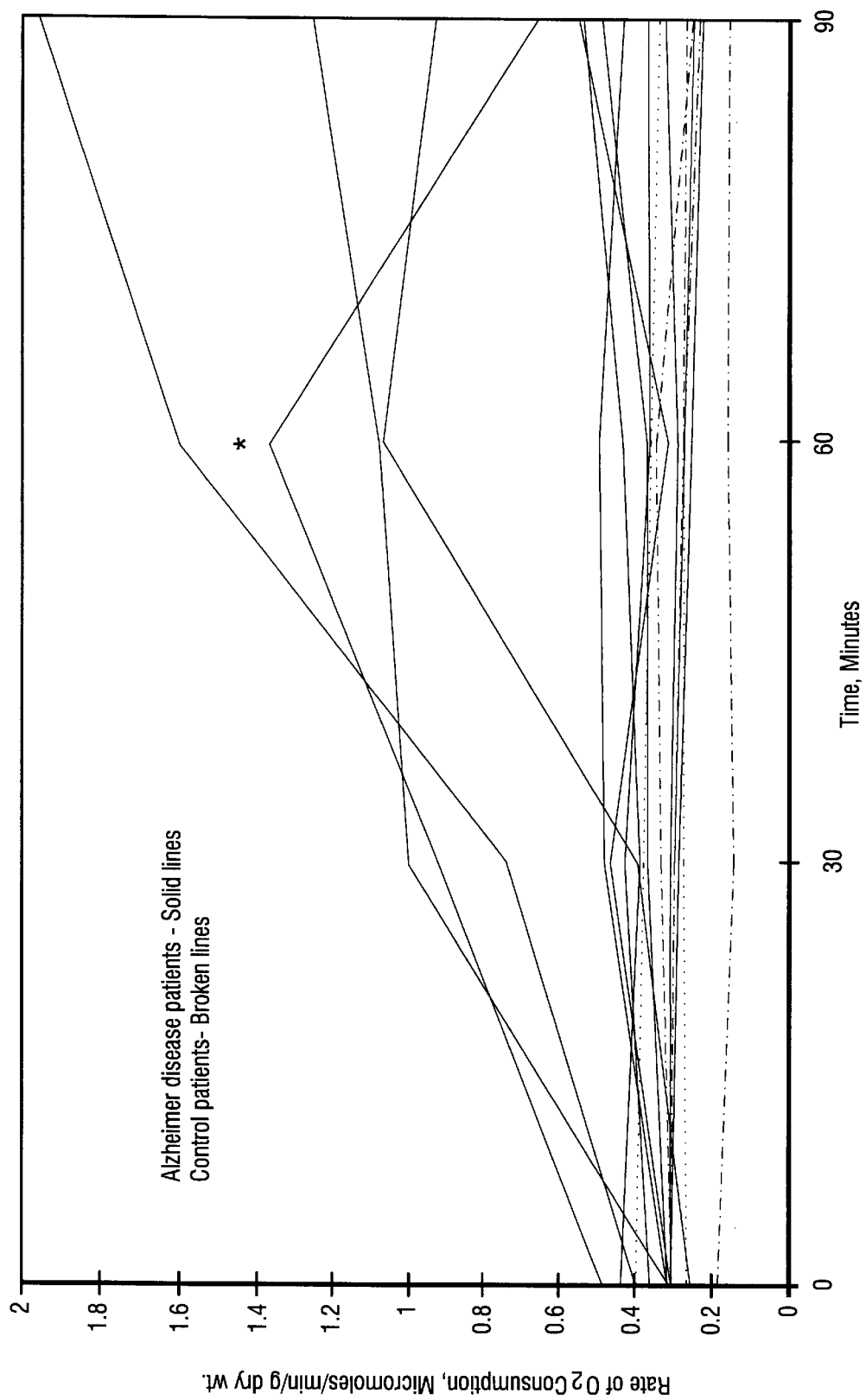
FIG. 14 shows actual oxygen consumption (micromoles/min/g dry weight) by porcine carotid arteries in the presence of CSF from individual Alzheimer's disease and control patients. The * marks the point at which in a test with CSF from an Alzheimer Disease patient, the CSF is rinsed away.

FIG. 14 shows the actual respiration rates for porcine carotid arteries exposed to CSF from each individual Alzheimer's Disease and control patient. The * marks the point at which in a test with CSF from an Alzheimer disease patient, the CSF was rinsed away. The removal of CSF from an Alzheimer's Disease patient caused the respiration rate to rapidly fall, reaching about the rate of CSF from control patients within about 30 mins. This effect of removal of Alzheimer's Disease CSF on respiration rate is similar to that observed using serum from pre-eclampsia patients and distinct to the effect observed using CSF or serum from sub-arachnoid haemorrhage patients.

The above provides demonstration of a vasoactive agent in CSF of Alzheimer's Disease patients. There has been no previous suggestion of a vasoactive eg vasoconstrictive agent being involved in Alzheimer's Disease.

The fact that the effects caused by CSf from Alzheimer's disease patients are reversible, indicates that the spasminogen(s) concerned can be dissociated from its receptor or binding site. The OxBox system also allows for the identification and manufacture of molecular entities which are structurally related to the spasminogen (eg analogues thereof) which although able to bind to the receptor/binding site for the spasminogen do not stimulate the pathological effects. Any such molecular entities are likely to be of practical value as drugs.

A screen for such molecular entities eg analogues may be carried out with or without specific knowledge of the nature of the spasminogen for a pathological effect. Various screening approaches may be employed. For example, the OxBox system as described herein can be set up using CSF from an Alzheimer's disease patient to establish a positive respiratory response ie a significant rise in the rate of oxygen consumption. One can then add a molecular entity to the respiration solution and observe the rate of oxygen consumption. Since the spasminogen(s) associated with Alzheimer's disease can be dissociated from its receptor/binding site with a consequent drop in the rate of oxygen consumption, a drop in the rate of oxygen consumption caused by the addition of the molecular entity to the respiration solution, indicates that the molecular entity is able to compete with the spasminogen for binding to the spasminogen receptor/binding site.

Molecular entities with such effects are likely to be of value as treatment (prophylactic/therapeutic) agents.

One suitable screening approach is described above. Others will be apparent to those skilled in the art.

Such a screen as set out may be used to look for treatment agents in relation to other pathologies associated with spasminogenic agents eg pre-eclampsia.

A molecular entity identifies as being able to compete with a spasminogen for binding to the spasminogen receptor/binding site may be polypeptide, peptide or non-peptide in nature. Non-peptide "small molecules" are often preferred for many in vitro pharmaceutical uses. Accordingly, a mimetic or mimic of the substance (particularly if a peptide) may be designed for pharmaceutical use.

The designing of mimetics and structural analogues (such as antagonistic structural analogues) to a known pharmaceutically active compound is a known approach to the development of pharmaceuticals based on a "lead" compound (eg the molecular entity identified as being of interest by the OxBox system). This might be desirable where the active compound is difficult or expensive to synthesise or where it is unsuitable for a particular method of administration, e.g. peptides are unsuitable active agents for oral compositions as they tend to be quickly degraded by proteases in the alimentary canal. Mimetic design, synthesis and testing is generally used to avoid randomly screening large number of molecules for a target property.

There are several steps commonly taken in the design of a mimetic or structural analogue (such as an antagonistic structural analogue) from a compound having a given target property. Firstly, the particular parts of the compound that are critical and/or important in determining the target property are determined. In the case of a peptide, this can be done by systematically varying the amino acid residues in the peptide, eg by substituting each residue in turn. Alanine scans of peptide are commonly used to refine such peptide motifs. These parts or residues constituting the active region of the compound are known as its "pharmoacophore".

Once the pharmacophore has been found, its structure is modelled to according its physical properties, eg stereochemistry, bonding, size and/or charge, using data from a range of sources, eg spectroscopic techniques, X-ray diffraction data and NMR. Computational analysis, similarity mapping (which models the charge and/or volume of a pharmacophore, rather than the bonding between atoms) and other techniques can be used in this modelling process.

In a variant of this approach, the three-dimensional structure of the ligand and its binding partner are modelled. This can be especially useful where the ligand and/or binding partner change conformation on binding, allowing the model to take account of this in the design of the mimetic or structural analogue.

A template molecule is then selected onto which chemical groups which mimic the pharmacophore can be grafted. The template molecule and the chemical groups grafted on to it can conveniently be selected so that the mimetic is easy to synthesise, is likely to be pharmacologically acceptable, and does not degrade in vivo, while retaining the biological activity of the lead compound. Alternatively, where the mimetic is peptide based, further stability can be achieved by cyclising the peptide, increasing its rigidity. The mimetic or mimetics found by this approach can then be screened to see whether they have the target property, or to what extent they exhibit it. Further optimisation or modification can then be carried out to arrive at one or more final mimetics for in vivo or clinical testing.

Given the above, the present invention also provides molecular entities and treatment agents as set out above and readily and routinely available by the approaches as set out above, pharmaceuticals comprising such molecular entitites/treatment agents, uses of such molecular entities/treatment agents eg in screening systems, design of mimetics and structural analogues, formulation and use of pharmaceuticals.

What is claimed is:

1. A method for screening compounds for potential efficacy as therapeutic agents which comprises incubating, in a medium suitable for the support of oxidative metabolism, a cell or tissue sample which comprises smooth muscle cells with (a) a specimen, agent or combination of agents known to effect an increase in oxidative metabolism of the cell or tissue sample which is not attributable to a contractile demand for ATP; and (b) a test compound;

measuring a marker of oxidative metabolism; and detecting an absence or reduction of the increase in oxidative metabolism not attributable to a contractile demand for ATP and which is normally effected by the specimen, agent or combination of agents, any such absence or reduction being indicative of the test compound having potential efficacy as a therapeutic agent.

2. A method according to claim 1 wherein the cell or tissue sample comprises vascular smooth muscle cells.

3. A method in accordance with claim 1 wherein identification of a test compound having potential efficacy as a therapeutic agent includes preparation of a synthetic version or derivative of the test compound which substantially retains the biological activity of the test compound.

4. A method in accordance with claim 1 or 3 wherein identification of a test compound having potential efficacy as a therapeutic agent includes preparation of a synthetic version or derivative of the test compound, and wherein a pharmaceutical comprising said test compound or derivative in a therapeutically effective amount is prepared.

5. A method according to claim 1 wherein the specimen is selected from cerebral spinal fluid (CSF); blood, sera or plasma.

6. A method according to claim 1 wherein the marker of oxidative metabolism is selected from oxygen consumption rate, ATPase activity, kinase activity phosphorylation state of myosin or ADP concentration in the cell or tissue sample.

7. A method according to claim 1 wherein said medium comprises

Krebs buffer with 11 mM glucose and/or 5 mM pyruvate or
Krebs-Hensleit buffer containing 0.5 mM $KH_2PO_4$ with 11 mM glucose and/or 5 mM pyruvate.

8. A method according to claim 1 wherein said medium is free of viable microorganisms.

9. A method according to claim 1 wherein the incubation is aerated with 95% $O_2$ and 5% $CO_2$.

10. A method according to claim 1 wherein the incubating is conducted at a pH which supports oxidative metabolism of the cell or tissue sample.

11. A method according to claim 1 wherein the incubating is conducted a pH of at substantially 7.4.

* * * * *